(12) United States Patent
Molina

(10) Patent No.: US 11,129,728 B1
(45) Date of Patent: Sep. 28, 2021

(54) SURGICALLY IMPLANTABLE JOINT SPACER

(71) Applicant: Guillermo Molina, Miami, FL (US)

(72) Inventor: Guillermo Molina, Miami, FL (US)

( * ) Notice: Subject to any disclaimer, the term of this patent is extended or adjusted under 35 U.S.C. 154(b) by 135 days.

(21) Appl. No.: 16/681,812

(22) Filed: Nov. 12, 2019

Related U.S. Application Data

(60) Provisional application No. 62/740,933, filed on Oct. 3, 2018.

(51) Int. Cl.
*A61F 2/44* (2006.01)
*A61F 2/46* (2006.01)
*A61F 2/30* (2006.01)

(52) U.S. Cl.
CPC .............. *A61F 2/442* (2013.01); *A61F 2/447* (2013.01); *A61F 2/4611* (2013.01); *A61F 2002/30476* (2013.01); *A61F 2002/30556* (2013.01); *A61F 2002/30579* (2013.01); *A61F 2002/30733* (2013.01)

(58) Field of Classification Search
CPC ........ A61F 2/4425; A61F 2/442; A61F 2/443; A61F 2/4435; A61F 2/4455; A61F 2/446; A61F 2/4465; A61F 2/447
See application file for complete search history.

(56) References Cited

U.S. PATENT DOCUMENTS

| | | | |
|---|---|---|---|
| 5,059,193 A | 10/1991 | Kuslich | |
| 5,116,357 A | 5/1992 | Eberbach | |
| 5,147,374 A | 9/1992 | Fernandez | |
| 5,160,323 A | 11/1992 | Andrew | |
| 5,171,278 A | 12/1992 | Pisharodi | |
| 5,195,505 A | 3/1993 | Josefsen | |
| 5,199,419 A | 4/1993 | Remiszewski et al. | |
| 5,245,987 A | 9/1993 | Redmond et al. | |
| 5,381,788 A | 1/1995 | Matula et al. | |
| 5,456,695 A | 10/1995 | Herve Dallemagne | |
| 5,514,157 A | 5/1996 | Nicholas et al. | |
| 5,554,101 A | 9/1996 | Matula et al. | |
| 5,662,702 A | 9/1997 | Keranen | |

(Continued)

FOREIGN PATENT DOCUMENTS

| | | |
|---|---|---|
| EP | 1259179 | 11/2002 |
| EP | 1928332 | 6/2008 |

(Continued)

*Primary Examiner* — Matthew J Lawson
(74) *Attorney, Agent, or Firm* — Allen D Hertz, P.A.; Allen D. Hertz

(57) ABSTRACT

A surgically implantable spacer including a primary body, a normal positioning member, and a translative positioning and locking control member. The normal positioning member is slideably assembled to the primary body, wherein the normal positioning member slides in a normal direction. The locking control member is slideably assembled to the normal positioning member. Projections of the locking control member seat in one of a series of positioning notches. The series of positioning notches are arranged in a stair step arrangement. As the locking control member is driven forward, the locking control member is raised by the projection and notch arrangement, thus raising the normal positioning member. This motion increases a span between a bottom surface and a top surface of the surgically implantable spacer.

20 Claims, 16 Drawing Sheets

(56) References Cited

U.S. PATENT DOCUMENTS

| | | |
|---|---|---|
| 5,683,449 A | 11/1997 | Marcade |
| 5,693,100 A | 12/1997 | Pisharodi |
| 5,722,935 A | 3/1998 | Christian |
| 5,755,769 A | 5/1998 | Richard et al. |
| 5,769,884 A | 6/1998 | Solovay |
| 5,800,526 A | 9/1998 | Anderson |
| 5,928,239 A | 7/1999 | Mirza |
| 5,948,002 A | 9/1999 | Bonutti |
| 6,077,297 A | 6/2000 | Robinson et al. |
| 6,395,035 B2 | 5/2002 | Bresina |
| 6,425,887 B1 | 7/2002 | McGuckin et al. |
| 6,592,559 B1 | 7/2003 | Pakter et al. |
| 6,595,998 B2 | 7/2003 | Johnson et al. |
| 6,746,451 B2 | 6/2004 | Middleton et al. |
| 6,923,813 B2 | 8/2005 | Phillips et al. |
| 6,939,369 B2 | 9/2005 | Osborne et al. |
| 7,070,598 B2 | 7/2006 | Um |
| 7,166,131 B2 | 1/2007 | Studer et al. |
| 7,226,474 B2 | 6/2007 | Iancea et al. |
| 7,238,186 B2 | 7/2007 | Zdeblick |
| 7,608,100 B2 | 10/2009 | Osborne et al. |
| 7,645,301 B2 | 1/2010 | Hudgins |
| 7,666,226 B2 | 2/2010 | Schaller |
| 7,758,647 B2 | 7/2010 | Arnin et al. |
| 7,857,857 B2 | 12/2010 | Kim |
| 7,955,384 B2 | 6/2011 | Rafiee |
| 7,959,652 B2 | 6/2011 | Zucherman |
| 8,097,018 B2 | 1/2012 | Malandain |
| 8,206,291 B2 | 6/2012 | Fischvogt et al. |
| 8,231,639 B2 | 7/2012 | Bolduc et al. |
| 8,231,678 B2 | 7/2012 | Lambrecht |
| 8,236,055 B2 | 8/2012 | Cordaro |
| 8,439,972 B2 | 5/2013 | Badawi |
| 8,465,494 B2 | 6/2013 | Butler et al. |
| 8,470,043 B2 | 6/2013 | Schaller et al. |
| 8,529,628 B2 | 9/2013 | Marino |
| 8,641,769 B2 | 2/2014 | Malandain |
| 8,778,027 B2 | 7/2014 | Medina |
| 8,795,369 B1* | 8/2014 | Pimenta .............. A61F 2/44 623/17.11 |
| 9,320,611 B2 | 4/2016 | Rodriguez |
| 10,258,480 B1 | 4/2019 | Rodriguez |
| 2003/0074063 A1* | 4/2003 | Gerbec .............. A61F 2/4637 623/16.11 |
| 2003/0176911 A1 | 9/2003 | Lancea et al. |
| 2003/0191517 A1 | 10/2003 | Osborne et al. |
| 2004/0117004 A1 | 6/2004 | Osborne et al. |
| 2004/0186354 A1 | 9/2004 | LiDonnici |
| 2004/0267269 A1 | 12/2004 | Middleton et al. |
| 2005/0240193 A1 | 10/2005 | Layne et al. |
| 2006/0149306 A1 | 7/2006 | Hart et al. |
| 2006/0282166 A1 | 12/2006 | Molz et al. |
| 2006/0293753 A1 | 12/2006 | Thramann |
| 2007/0168041 A1 | 7/2007 | Kadiyala |
| 2007/0276462 A1 | 11/2007 | Iancea et al. |
| 2008/0021559 A1* | 1/2008 | Thramann .............. A61F 2/447 623/17.16 |
| 2008/0039877 A1 | 2/2008 | Kammerer |
| 2008/0114364 A1 | 5/2008 | Goldin et al. |
| 2008/0140084 A1 | 6/2008 | Osorio et al. |
| 2008/0140203 A1 | 6/2008 | Davis |
| 2008/0161847 A1 | 7/2008 | Sandhu et al. |
| 2008/0183044 A1 | 7/2008 | Colleran et al. |
| 2008/0242940 A1 | 10/2008 | Stefanchik |
| 2008/0281364 A1 | 11/2008 | Chirico et al. |
| 2009/0012564 A1 | 1/2009 | Chirico et al. |
| 2009/0118836 A1 | 5/2009 | Cordaro |
| 2009/0138043 A1 | 5/2009 | Kohm |
| 2009/0148591 A1 | 6/2009 | Wang et al. |
| 2009/0163918 A1 | 6/2009 | Levy |
| 2009/0204216 A1 | 8/2009 | Biedermann et al. |
| 2009/0326461 A1 | 12/2009 | Gresham |
| 2010/0063548 A1 | 3/2010 | Wang |
| 2010/0076445 A1 | 3/2010 | Pagano |
| 2010/0130824 A1 | 5/2010 | Piskun |
| 2010/0174267 A1 | 7/2010 | McGuckin, Jr. |
| 2010/0185161 A1 | 7/2010 | Pellegrino et al. |
| 2010/0228289 A1 | 9/2010 | Park |
| 2010/0280622 A1* | 11/2010 | McKinley .............. A61F 2/4611 623/17.16 |
| 2011/0004308 A1 | 1/2011 | Marino et al. |
| 2011/0054260 A1 | 3/2011 | Albrecht et al. |
| 2011/0054538 A1 | 3/2011 | Zehavi et al. |
| 2011/0093075 A1 | 4/2011 | Duplesis et al. |
| 2011/0245926 A1 | 10/2011 | Kitchen |
| 2012/0116520 A1 | 5/2012 | Cauthen, III et al. |
| 2013/0116791 A1* | 5/2013 | Theofilos .............. A61F 2/4611 623/17.16 |
| 2013/0123927 A1 | 5/2013 | Malandain |
| 2017/0239062 A1* | 8/2017 | Williams .............. A61F 2/4611 |
| 2019/0282377 A1* | 9/2019 | McLean .............. A61F 2/447 |

FOREIGN PATENT DOCUMENTS

| | | |
|---|---|---|
| WO | WO 2005/097006 | 10/2005 |
| WO | WO 2007/002602 | 1/2007 |
| WO | WO 2007/117908 | 10/2007 |
| WO | WO 2008/022206 | 2/2008 |

\* cited by examiner

SURGICALLY IMPLANTABLE JOINT SPACER

CROSS REFERENCE TO RELATED APPLICATIONS

This application is a Non-Provisional Utility Application claiming the benefit of U.S. Provisional Patent Application Ser. No. 62/740,933, filed on Oct. 3, 2018, which is incorporated by reference herein in its entirety.

FIELD OF THE INVENTION

The present disclosure generally relates to a medically implanted spacer. More particularly, the present disclosure relates to a medically implanted spacer for insertion within a joint formed between two adjacent bones to enhance movement or fuse in a deteriorated biological joint. In one exemplary embodiment, the two adjacent bones are vertebra.

BACKGROUND OF THE INVENTION

Biological joints can degrade over time, deteriorate as a result of a birth defect or a disease, become damaged as a result of an accident or unwarranted motion, malformations due to incorrect growths, and the like. As the joint deviates from a normal, mobile condition, the malformed joint can cause multiple issues to the individual or animal, including sporadic pain or constant pain, limited motion, any degree of incapacitation, and the like.

Common joints that require surgical attention include inter-vertebrae discs, hips, knees, shoulders, elbows, and the like.

Inter-vertebrae discs can degrade over time or become damaged where they no longer function properly. The defective inter-vertebrae discs allow unwarranted motion between two adjacent vertebrae. The defective inter-vertebrae discs limit or reduce the support along the individual's spine. Over time, the defective inter-vertebrae disc needs surgical attention. Inter-vertebrae discs are addressed by fusing two or more adjacent vertebrae together. One short-term drawback of this procedure is the resulting limitation of motion incurred by the individual. A long-term drawback is that over time, the fused region increases stresses on adjacent joints, resulting in additional surgical procedures to fuse other regions of the individual's spine.

Other joints, such as hips and shoulders, are commonly formed having a first end of one bone moveably engaged with a mating end of a mating bone. Most joints comprise a first joint member formed in a ball and the mating joint member formed in a socket. As either or both of the surfaces of the joint members wears or deteriorates, the support of the joint degrades, hindering the mobility of the individual. In addition to the reduced mobility, the deteriorating joint can cause inflammation, discomfort, and other unwanted physical and psychological issues.

The surgically implantable device must meet certain criteria. The surgically implantable device must be expandable. The surgically implantable device must be capable of locking into an expanded configuration. The surgically implantable device to be inserted into a joint while passing through a small opening, then expand into a configuration which provides support across the subject joint.

Therefore, what is desired is a device capable of being surgically implanted to repair or overcome medial deficiencies of a damaged or defective biological joint.

SUMMARY OF THE INVENTION

The present disclosure is generally directed to a surgically implanted spacer for use in a joint formed between adjoining ends of two bones.

In a first aspect, the surgically implantable spacer may include:
a primary body having an elongated dimension extending along a longitudinal axis, a width dimension extending along a lateral axis, and a height dimension extending along a normal axis;
a primary body top flange extending generally along the lateral axis from an end of a width dimension of the primary body towards an interior of the primary body from an edge of the primary body;
a normal positioning member slideably assembled to the primary body along the normal axis;
a translative positioning and locking control member slideably assembled to the normal positioning member along the longitudinal axis; and
a normal direction interface between the translative positioning and locking control member and the primary body,
wherein the normal direction interface is configured to move the translative positioning and locking control member in a direction of the normal axis when the translative positioning and locking control member is slideably inserted into the normal positioning member in a direction of the longitudinal axis,
wherein the translative positioning and locking control member is configured to move the normal positioning member in the direction of the normal axis to a position along in a normal direction where a height dimension of a combination of the normal positioning member and the primary body is greater than the height dimension of the primary body,
wherein the primary body top flange is configured to limit the movement of the translative positioning and locking control member in the direction of the normal axis.

In a second aspect, when the translative positioning and locking control member is at a lowest position respective to the height dimension of the primary body, the height dimension of the combination of the normal positioning member and the primary body is one of substantially equal to or equal to the height dimension of the primary body.

In another aspect, the normal positioning member can include a clearance having a shape and size that circumscribes the primary body top flange, wherein the clearance enables movement of the normal positioning member in the direction of the normal axis passing the primary body top flange.

In yet another aspect, the primary body includes a primary body insertion end flange located at an insertion end of the primary body in the elongated dimension. The primary body insertion end flange is of a size and shape enabling insertion of the translative positioning and locking control member between a respective end of the primary body insertion end flange and an interior surface of the primary body top flange when inserted in a direction of the longitudinal axis.

In yet another aspect, the normal direction interface can include a series of translative positioning notches integral with the primary body, the series of translative positioning notches being in an inclined arrangement.

In yet another aspect, the surgically implantable spacer additionally includes retention ridges formed on an external surface of at least one of the primary body and the normal positioning member.

In yet another aspect, the surgically implantable spacer additionally includes a sliding engagement interface provided between the translative positioning and locking control member and the normal positioning member enabling a sliding movement along the longitudinal axis while refraining from movement respective to one another along the normal axis.

In yet another aspect, the surgically implantable spacer additionally includes at least one insertion grip feature provided on the primary body.

In a more detailed aspect, the surgically implantable spacer may include:
- a primary body having an elongated dimension extending along a longitudinal axis, a width dimension extending along a lateral axis, and a height dimension extending along a normal axis, the primary body including a pair of sidewalls, each sidewall extending upward from opposite edges of a base wall along the elongated dimension thereof;
- a primary body top flange extending generally along the lateral axis from a respective sidewall of the pair of sidewalls towards an interior of the primary body,
- a normal positioning member slideably assembled to the primary body along the normal axis; and
- a translative positioning and locking control member slideably assembled to the normal positioning member along the longitudinal axis;
- a normal direction interface between the translative positioning and locking control member and the primary body;
- wherein the normal direction interface is configured to move the translative positioning and locking control member in a direction of the normal axis when the translative positioning and locking control member is slideably inserted into the normal positioning member in a direction of the longitudinal axis,
- wherein the translative positioning and locking control member is configured to move the normal positioning member in the direction of the normal axis,
- wherein the primary body top flange is configured to limit the movement of the translative positioning and locking control member in the direction of the normal axis.

In another more detailed aspect, the surgically implantable spacer may include:
- a primary body comprising:
  - a first primary body side panel, a second primary body side panel being substantially parallel to the first primary body side panel a primary body distal end panel extending between a distal end of the first primary body side panel and a distal end the second primary body side panel, and a primary body insertion end flange having a first portion extending inward from an insertion end of the first primary body side panel and a second portion extending inward from an insertion end the second primary body side panel,
  - a first series of primary body proximal translative positioning notches proximate an interior surface of the first primary body side panel at a location adjacent to the insertion end of the first primary body side panel,
  - a second series of primary body proximal translative positioning notches proximate an interior surface of the second primary body side panel at a location adjacent to the insertion end of the second primary body side panel,
  - a first series of primary body distal translative positioning notches proximate the interior surface of the first primary body side panel at a location adjacent to the distal end of the first primary body side panel, and
  - a second series of primary body distal translative positioning notches proximate the interior surface of the second primary body side panel at a location adjacent to the distal end of the second primary body side panel;
- a normal positioning member comprising:
  - a normal positioning member top panel,
  - a pair of normal positioning member side panels extending from the normal positioning member top panel in an orientation that is substantially perpendicularly to the normal positioning member top panel, and
  - a normal positioning member elongated formation extending on an interior surface of each normal positioning member side panel of the pair of normal positioning member side panels in a longitudinal direction; and
- a translative positioning and locking control member comprising:
  - a translative positioning and locking control member body,
  - a translative positioning member elongated formation extending on an exterior elongated surface of the translative positioning and locking control member body, each control member body laterally positioning member elongated formation being located, sized and shaped to slideably engage with the laterally positioning member elongated formation on each respective laterally positioning member side panel of the pair of laterally positioning member side panels,
  - a series of translative positioning and locking control member notch engaging projections, each translative positioning and locking control member notch engaging projection of the series of translative positioning and locking control member notch engaging projections being located on the translative positioning and locking control member to engage with a respective notch of the respective series of primary body distal translative positioning notches,
- wherein the normal positioning member normally is slideably assembled to the primary body providing a sliding translative motion between the laterally positioning member and the primary body in a generally transverse direction,
- wherein each control member body laterally positioning member elongated formation is slideably assembled to the respective normal positioning member elongated formation;
- wherein each translative positioning and locking control member notch engaging projection of the series of translative positioning and locking control member notch engaging projections engages with the translative positioning and locking control member to engage with a respective notch of the respective series of primary body distal translative positioning notches.

In a second aspect, a first referenced orientation of the surgically implantable spacer can be identified as an elongated axis or a longitudinal axis extending along an elongated direction or a longitudinal direction of the surgically implantable spacer.

In another aspect, a second referenced orientation of the surgically implantable spacer can be identified as a lateral axis extending along a lateral direction of the surgically implantable spacer, where the lateral direction is perpendicular to the longitudinal axis in a first direction.

In yet another aspect, a third referenced orientation of the surgically implantable spacer can be identified as a normal axis extending along a direction that is perpendicular to a plane defined by the longitudinal axis and the lateral axis.

In yet another aspect, the components of the surgically implantable spacer are fabricated of a biologically compatible and structurally supporting material.

In yet another aspect, the components of the surgically implantable spacer are fabricated of a biologically compatible and structurally supporting material, such as metal or metal alloys including stainless steel, titanium (Ti), and cobalt-chrome (CoCr) alloy, polymers such as ultrahigh molecular weight polyethylene (UHMWPE), and the like.

In yet another aspect, at least a portion of the surface of at least one component can be coated to improve this type of bony ingrowth and include titanium wire mesh, plasma-sprayed titanium, porous CoCr, and bioactive materials such as hydroxyapatite and calcium phosphate.

In yet another aspect, the surgically implantable spacer is assembled by slidably assembling the primary body and the normal positioning member to one another along a normal axis.

In yet another aspect, the surgically implantable spacer is assembled by slidably assembling the translative positioning and locking control member and the normal positioning member to one another along a longitudinal axis.

In yet another aspect, one or more of the notch engaging projections is formed having a rounded notch engaging surface.

In yet another aspect, the normal positioning member top panel includes an arched exterior surface.

In yet another aspect, the normal positioning member top panel includes an arched exterior surface, the arched surface being convex.

In yet another aspect, the primary body further comprises a bottom structure.

In yet another aspect, the primary body bottom structure includes an exterior surface that is planar.

In yet another aspect, the primary body bottom structure includes an exterior surface that has an arched shape.

In yet another aspect, the primary body bottom structure includes an exterior surface that has a convex arched shape.

In yet another aspect, the primary body bottom structure includes an exterior surface having a plurality of primary body retention features.

In yet another aspect, wherein the primary body retention features are provided in a formation of retention ridges.

In yet another aspect, the primary body bottom structure includes an exterior surface having a plurality of primary body retention ridges, wherein each normal positioning member retention ridge of the plurality of primary body retention ridges is oriented having a side sloping upwards from a distal end towards an insertion end to provide easy insertion and difficult removal.

In yet another aspect, the primary body bottom structure includes an exterior surface having a plurality of primary body retention ridges, further comprising a passageway between adjacent primary body retention ridges.

In yet another aspect, a gap defined by adjacent primary body retention ridges of the plurality of primary body retention ridges is consistent between each pair of adjacent primary body retention ridges of the plurality of primary body retention ridges.

In yet another aspect, the normal positioning member top panel includes an exterior surface having a plurality of primary body retention ridges.

In yet another aspect, the normal positioning member top panel includes an exterior surface having a plurality of primary body retention ridges, wherein each normal positioning member retention ridge of the plurality of primary body retention ridges is oriented having a side sloping upwards from a distal end towards an insertion end to provide easy insertion and difficult removal.

In yet another aspect, the normal positioning member top panel includes an exterior surface having a plurality of primary body retention ridges, further comprising a passageway between adjacent primary body retention ridges.

In yet another aspect, a gap defined by adjacent primary body retention ridges of the plurality of primary body retention ridges is consistent between each pair of adjacent primary body retention ridges of the plurality of primary body retention ridges.

In yet another aspect, a gap defined between a first pair of adjacent primary body retention ridges of the plurality of primary body retention ridges differs from a gap defined between a second pair of adjacent primary body retention ridges of the plurality of primary body retention ridges.

In yet another aspect, the normal positioning member elongated formation of the normal positioning member is provided in a form of a groove.

In yet another aspect, the normal positioning member elongated formation of the translative positioning and locking control member is provided in a form of a projection extending in the elongated direction, sometimes referred to as a tail.

In yet another aspect, the normal positioning member elongated formation of the normal positioning member is provided in a form of a groove and the normal positioning member elongated formation of the translative positioning and locking control member is provided in a form of a projection extending in the elongated direction, sometimes referred to as a tail, wherein the tail and the groove are slideably assembled to one another.

In yet another aspect, the normal positioning member elongated formation of the normal positioning member is provided in a form of a projection extending in the elongated direction, sometimes referred to as a tail.

In yet another aspect, the normal positioning member elongated formation of the translative positioning and locking control member is provided in a form of a groove.

In yet another aspect, the normal positioning member elongated formation of the normal positioning member is provided in a form of a projection extending in the elongated direction, sometimes referred to as a tail and the normal positioning member elongated formation of the translative positioning and locking control member is provided in a form of a groove, wherein the groove and the tail are slideably assembled to one another.

In yet another aspect, the primary body further comprising a normally translative limiting feature.

In yet another aspect, the translative positioning and locking control member further comprising a normally translative limiting feature.

In yet another aspect, the normally translative limiting feature of the primary body and the normally translative limiting feature of the translative positioning and locking control member are designed to engage with one another to limit a normal sliding motion of the normal positioning member top panel.

In yet another aspect, each normally translative limiting feature of the primary body is formed as a flange extending inward from a respective interior surface of the respective first or second primary body side panel.

In yet another aspect, each normally translative limiting feature of the primary body is formed as a flange extending in a lateral direction from a respective interior surface of the respective first or second primary body side panel.

In yet another aspect, each normally translative limiting feature of the primary body is formed as a flange extending inward in a lateral direction from a respective interior surface of the respective first or second primary body side panel.

In yet another aspect, each normally translative limiting feature of the primary body is formed as a flange extending inward in a direction that is substantially parallel to a plane defined by the longitudinal axis and the lateral axis from a respective interior surface of the respective first or second primary body side panel.

In yet another aspect, each normally translative limiting feature of the primary body is formed as a flange extending inward from a respective interior surface of the respective first or second primary body side panel, the flange having a length in a longitudinal direction between a first flange lateral edge and a second flange lateral edge.

In yet another aspect, each normally translative limiting feature of the primary body is formed as a flange extending inward from a respective interior surface of the respective first or second primary body side panel generally along a plane defined by longitudinal axis and the lateral axis, the flange having a length in a longitudinal direction between a first flange lateral edge and a second flange lateral edge.

In yet another aspect, each normally translative limiting feature of the primary body is formed as a flange extending inward from a respective interior surface of the respective first or second primary body side panel, the flange having a length in a longitudinal direction between a first flange lateral edge and a second flange lateral edge, wherein each of the first flange lateral edge and the second flange lateral edge generally extending along a lateral axis.

In yet another aspect, each normally translative limiting feature of the primary body is formed as a flange extending inward from a respective interior surface of the respective first or second primary body side panel, the flange having a length in a longitudinal direction between a first flange lateral edge and a second flange lateral edge, wherein each of the first flange lateral edge and the second flange lateral edge generally extending along a plane defined by the lateral axis and the normal axis.

In yet another aspect, each normally translative limiting feature of the translative positioning and locking control member is formed as a flange extending outward from an exterior surface of the respective elongated or longitudinal edge translative positioning and locking control member.

In yet another aspect, each normally translative limiting feature of the translative positioning and locking control member is formed as a flange extending outward from an exterior surface of the respective elongated or longitudinal edge translative positioning and locking control member, the normally translative limiting feature extending between a distal notch engaging projection and a proximal notch engaging projection of the same side of the translative positioning and locking control member.

In yet another aspect, the normal positioning member top panel further comprises a normal positioning member guide feature, the primary body further comprising a normal positioning member guide feature, wherein the normal positioning member guide feature of the normal positioning member top panel is designed to and engages with the normal positioning member guide feature of the primary body.

In yet another aspect, each normally translative limiting feature of the translative positioning and locking control member is located below a translative positioning and locking control member top section of the translative positioning and locking control member.

In yet another aspect, each normally translative limiting feature of the translative positioning and locking control member is located below an elongated side edge of the translative positioning and locking control member.

In yet another aspect, the translative positioning and locking control member includes a translative positioning and locking control member elongated axis beltline located between the translative positioning and locking control member top section elongated side edge and the translative positioning and locking control member base flange (the normally translative limiting feature).

In yet another aspect, the normal positioning member guide feature of the normal positioning member top panel is provided in a form of a normally oriented surface.

In yet another aspect, the normal positioning member guide feature of the normal positioning member top panel engages with the vertically translative limiting feature of the primary body.

In yet another aspect, the normal positioning member guide feature of the normal positioning member top panel engages with an edge of the vertically translative limiting feature of the primary body.

In yet another aspect, the normal positioning member guide feature of the normal positioning member top panel is provided in a form of a normally oriented surface, wherein the normally oriented surface extending along a plane defined by the lateral axis and the normal axis.

In yet another aspect, the normal positioning member guide feature of the normal positioning member top panel engages with an edge of the vertically translative limiting feature of the primary body, wherein the edge of the vertically translative limiting feature of the primary body extends along a lateral axis.

In yet another aspect, the normal positioning member guide feature of the normal positioning member top panel engages with a surface of the vertically translative limiting feature of the primary body, wherein the surface of the vertically translative limiting feature of the primary body extends along a plane defined by the lateral axis and the normal axis.

In yet another aspect, each translative positioning and locking control member of the series of translative positioning and locking control members is arranged in a stair stepping manner with an adjacent translative positioning and locking control member.

In yet another aspect, each translative positioning and locking control member is formed having a seating section, a rising section, and a locking feature.

In yet another aspect, each translative positioning and locking control member is formed having a seating section, a rising section, and a locking feature, wherein the transition between the seating section and the rising section is arched.

In yet another aspect, each translative positioning and locking control member is formed having a seating section, a rising section, and a locking feature, wherein the transition between the rising section and the locking feature is arched.

In yet another aspect, each translative positioning and locking control member is formed having a seating section, a rising section, and a locking feature, wherein the transition between the seating section, the rising section and the locking feature is arched.

In yet another aspect, each translative positioning and locking control member is formed having a seating section, a rising section, and a locking feature, wherein the transition between the seating section, the rising section and the locking feature is circular in shape.

In yet another aspect, each translative positioning and locking control member is formed having a seating section, a rising section, and a locking feature, wherein the transition between the seating section, the rising section and the locking feature is semi-spherical in shape.

In yet another aspect, the surgically implantable spacer further comprises at least one manipulation gripping feature.

In yet another aspect, the at least one manipulation gripping feature includes at least one orifice passing through the primary body side panel of the primary body.

In yet another aspect, the at least one manipulation gripping feature includes at least one bore formed within a primary body side panel of the primary body, wherein the bore only partially penetrates the primary body side panel of the primary body.

In yet another aspect, the at least one manipulation gripping feature is provided having a circular shape.

In yet another aspect, the at least one manipulation gripping feature is provided having an oblong shape.

In yet another aspect, the surgically implantable spacer further comprises at least two manipulation gripping features.

In yet another aspect, the surgically implantable spacer further comprises at least two manipulation gripping features, wherein at least one manipulation gripping feature of the at least two manipulation gripping features is formed having a circular shape.

In yet another aspect, the surgically implantable spacer further comprises at least two manipulation gripping features, wherein at least one manipulation gripping feature of the at least two manipulation gripping features is formed having an oblong shape.

In yet another aspect, the surgically implantable spacer further comprises at least two manipulation gripping features, wherein a first of the at least one manipulation gripping feature of the at least two manipulation gripping features is formed having a circular shape and another of the at least two manipulation gripping features is formed having an oblong shape.

In yet another aspect, the surgically implantable spacer further comprises at least two manipulation gripping features, wherein a first of the at least one manipulation gripping feature of the at least two manipulation gripping features is formed having a circular shape and the remaining manipulation gripping feature/features of the at least two manipulation gripping features is/are formed having an oblong shape.

In yet another aspect, the surgically implantable spacer further comprises at least two manipulation gripping features, wherein at least one manipulation gripping feature of the at least two manipulation gripping features is formed as a bore, wherein the bore only partially penetrates the respective primary body side panel.

In yet another aspect, the surgically implantable spacer further comprises at least two manipulation gripping features, wherein at least one manipulation gripping feature of the at least two manipulation gripping features is formed as an orifice, wherein the orifice passes through the respective primary body side panel.

In yet another aspect, the surgically implantable spacer further comprises at least two manipulation gripping features, wherein one or more manipulation gripping feature of the at least two manipulation gripping features is formed as an orifice, wherein the orifice passes through the respective primary body side panel and wherein at least a second or more manipulation gripping feature of the at least two manipulation gripping features is formed as a bore, wherein the bore only partially penetrates the respective primary body side panel.

In yet another aspect, the surgically implantable spacer further comprises two series of manipulation gripping features; each series is formed in/through an exterior surface of the respective primary body side panel.

In yet another aspect, the surgically implantable spacer further comprises two series of manipulation gripping features, each series is formed in/through an exterior surface of the respective primary body side panel, wherein a first of the two series of manipulation gripping features is formed in/through an exterior surface of the first primary body side panel and a second of the two series of manipulation gripping features is formed in/through an exterior surface of the second primary body side panel.

In yet another aspect, the surgically implantable spacer further comprises two series of manipulation gripping features, each series is formed in/through an exterior surface of the respective primary body side panel, wherein a first of the two series of manipulation gripping features is formed in/through an exterior surface of the first primary body side panel and a second of the two series of manipulation gripping features is formed in/through an exterior surface of the second primary body side panel, the first of the two series of manipulation gripping features and the second of the two series of manipulation gripping features are like one another.

In yet another aspect, the surgically implantable spacer further comprises two series of manipulation gripping features, each series is formed in/through an exterior surface of the respective primary body side panel, wherein a first of the two series of manipulation gripping features is formed in/through an exterior surface of the first primary body side panel and a second of the two series of manipulation gripping features is formed in/through an exterior surface of the second primary body side panel, the first of the two series of manipulation gripping features and the second of the two series of manipulation gripping features differ from one another.

In yet another aspect, the manipulation gripping features described as having an oblong shape is formed having an elongated shape.

In yet another aspect, an installation tool includes at least one element having a size and shape to engage with the at least one manipulation gripping feature.

In yet another aspect, an installation tool includes at least one projection having a size and shape to engage with the at least one manipulation gripping feature.

In yet another aspect, an installation tool includes at least one projection having a size and shape to snugly engage with one of the at least one manipulation gripping feature.

In yet another aspect, an installation tool includes at least one projection, each of the at least one projection having a size and shape to snugly engage with one or more of the at least one manipulation gripping feature.

In yet another aspect, an installation tool further including a translative component, wherein the translative component is designed to apply a force to the translative positioning and locking control member against a retention force applied to the primary body.

In yet another aspect, the surgically implantable spacer is configured into a collapsed configuration by positioning the notch engaging projections against an interior surface of the primary body bottom structure.

In yet another aspect, the surgically implantable spacer is configured into a collapsed configuration by positioning the notch engaging projections into the primary body translative positioning notches located closest to the primary body bottom structure.

In yet another aspect, the primary body further comprises:
a first insertion end flange extending inward from the insertion end of the respective side panel and oriented being substantially parallel to a plane defined by a lateral direction and a normal direction;
a second insertion end flange extending inward from the insertion end of the respective side panel and oriented being substantially parallel to a plane defined by a lateral direction and a normal direction,
the first insertion end flange and the second insertion end flange extending towards one another.

In yet another aspect, each of the first insertion end flange and the second insertion end flange extend upward or in a direction from an interior surface of the bottom component of the primary body.

In yet another aspect, each of the first insertion end flange and the second insertion end flange extend upward or in a direction from an interior surface of the bottom component of the primary body, terminating at an end that is distant from an edge of the respective side panel opposite the edge of the side panel proximate the bottom panel. The distance between the free end of each of the first insertion end flange and the second insertion end flange and the free edge of the side panel forming a gap. The gap being provided for receiving the translative positioning and locking control member. The first insertion end flange and the second insertion end flange are provided to retain the translative positioning and locking control member within the primary body once inserted, passing through the gap of the insertion flanges and each notch engaging projection being seated against the respective translative positioning notch.

In yet another aspect, a passageway is formed through a top section of the translative positioning and locking control member. The passageway reduces weight and provides a clearance for insertion of bone graft material.

In yet another aspect, the present invention discloses a method of use, the method comprising steps of:
obtaining a surgically implantable spacer, the surgically implantable spacer being described above;
inserting the surgically implantable spacer into a biological joint;
gripping the primary body of the surgically implantable spacer; and
applying a spacing force to the translative positioning and locking control member, the applied spacing force causing:
the notch engaging projections being forced upward along a rising section of the respective translative positioning notch to position the notch engaging projections onto a seating section of an adjacent translative positioning notch, wherein the adjacent translative positioning notch is at a further distance from an interior surface of the bottom component of the primary body compared to the previous translative positioning notch,
retaining each translative positioning notch in the respective seating section of the adjacent translative positioning notch using a translative positioning notch retention section.

In yet another aspect, the method further comprises a step of slideably engaging the elongated formation of the translative positioning and locking control member and the normal positioning member elongated formation of the normal positioning member with one another. The translative positioning and locking control member is slideably inserted into the primary body at a location on an interior side of a normal direction movement limiting feature of the primary body.

In yet another aspect, the method further comprises a step of limiting a movement of the normal positioning member in a normal direction by engaging a normal direction movement limiting feature of the translative positioning and locking control member with the normal direction movement limiting feature of the primary body.

In yet another aspect, the method further comprises a step of increasing a span between an exterior surface of a bottom component of the primary body and an exterior surface of the top panel of the normal positioning member.

In yet another aspect, the method further comprises a step of increasing a span between an exterior surface of a bottom component of the primary body and an exterior surface of the top panel of the normal positioning member, wherein as the span increases, the resistive pressure or force provided by the opposing surfaces of the respective projection, retaining the translative positioning and locking control member in position.

In yet another aspect, the method further comprises a step of applying bone graft to an interior of the surgically implantable spacer by injecting the bone graft through spaces or orifices formed between ridges on at least one of the normal positioning member top panel and the primary body bottom component.

These and other aspects, features, and advantages of the present invention will become more readily apparent from the attached drawings and the detailed description of the preferred embodiments, which follow.

BRIEF DESCRIPTION OF THE DRAWINGS

The invention will now be described, by way of example, with reference to the accompanying drawings, in which.

Like reference numerals refer to like parts throughout the several views of the drawings.

DETAILED DESCRIPTION OF THE INVENTION

Figure 1:
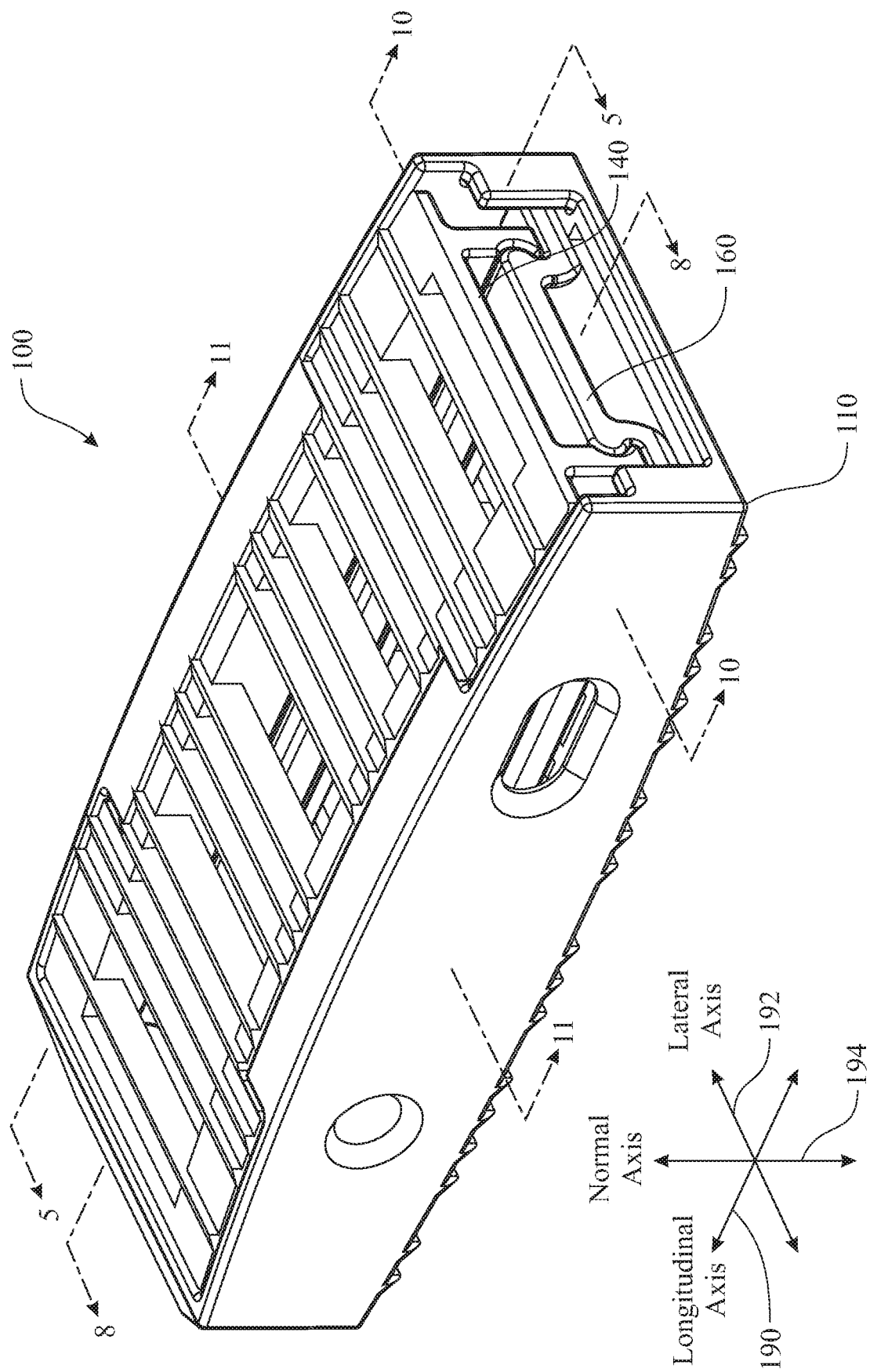
FIG. 1 presents an isometric top, side view of an exemplary surgically implantable spacer, the surgically implantable spacer being shown in a collapsed configuration.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention is generally directed towards a surgically implantable spacer 100, as illustrated in FIGS. 1 through 11. Orientation of the surgically implantable spacer 100 is referenced by an elongated axis 190, a lateral axis 192, and a normal axis 194.

The surgically implantable spacer 100 includes three components, a primary body 110, a normal positioning member 140 and a translative positioning and locking control member 160. The normal positioning member 140 is slideably assembled to the primary body 110, where the normal positioning member 140 slides in a direction substantially parallel to the normal axis 194. The translative positioning and locking control member 160 is slideably assembled to the normal positioning member 140, wherein the translative positioning and locking control member 160 slides in a direction that is substantially parallel to the elongated axis 190. The translative positioning and locking control member 160 provides a retention function, preventing separation of the normal positioning member 140 from the primary body 110. The translative positioning and locking control member 160 additionally provides a spacing function, where the translative positioning and locking control member 160 positions the normal positioning member 140 between an insertion configuration and a spaced configuration.

The components 110, 140, 160 of the surgically implantable spacer 100 can be fabricated of a biologically compatible and structurally supporting material. Examples of suitable biologically compatible and structurally supporting material include a metal or metal alloys including stainless steel, titanium (Ti), and cobalt-chrome (CoCr) alloy, polymers such as ultrahigh molecular weight polyethylene (UHMWPE), and the like. At least a portion of en exposed surface of at least one component 110, 140, 160 of the surgically implantable spacer 100 can be coated to improve this type of bony ingrowth and include titanium wire mesh, plasma-sprayed titanium, porous CoCr, and bioactive materials such as hydroxyapatite and calcium phosphate.

The primary body 110 provides a primary structure for operation of the normal positioning member 140 and the translative positioning and locking control member 160. Additionally, the exemplary primary body 110 provides one of two support surfaces. The exemplary primary body 110 includes a first primary body side panel 112 and a second primary body side panel 112. Each of the first primary body side panel 112 and the second primary body side panel 112 includes an interior surface and an exterior surface. Each of the first primary body side panel 112 and the second primary body side panel 112 is arranged being generally parallel to a plane defined by the elongated axis 190 and the normal axis 194. The first primary body side panel 112 and the second primary body side panel 112 are oriented having interior surfaces facing one another and preferably substantially parallel to one another. A primary body distal end panel 116 extends between distal ends of the first primary body side panel 112 and the second primary body side panel 112. The primary body distal end panel 116 is arranged being generally parallel to a plane defined by the lateral axis 192 and the normal axis 194. A primary body bottom structure 113 extends between lower or bottom edges of the first primary body side panel 112 and the second primary body side panel 112, as well as the lower or bottom edge of the primary body distal end panel 116. Collectively, interior surfaces of the first primary body side panel 112, the second primary body side panel 112, the primary body distal end panel 116 and the primary body bottom structure 113 define an interior cavity (not referenced).

The primary body 110 can include several features supporting operation of the surgically implantable spacer 100. One exemplary feature is an installation assisting feature. The exemplary surgically implantable spacer 100 includes a plurality of installation gripping features 122, 123. The gripping features 122, 123 can be created in any suitable shape or size. In the exemplary illustration, the gripping features 122, 123 are provided as a formation in each respective primary body side panel 112. The gripping features 122, 123 can be a partial bore, extending into the respective primary body side panel 112 from the exterior surface, a full bore or hole passing through the respective primary body side panel 112 from the exterior surface, a slot extending into the respective primary body side panel 112 from the exterior surface, a slot passing through the respective primary body side panel 112 from the exterior surface, or any other suitable formation. It is recognized that the gripping features 122, 123 can be of like shapes and sizes or different shapes and sizes. In the exemplary embodiment, the primary body proximal insertion grip feature 122 is formed as an oblong shaped slot passing through the respective primary body side panel 112 and the primary body distal insertion grip feature 123 is formed as a circular partial bore extending partially into the material of the primary body side panel 112. An advantage of using a circular shaped gripping feature in combination with a slotted gripping feature is that the design of the gripping features supports an insertion tool having a less accurate span between a first gripping element and a second gripping element. The gripping element that is inserted into the circular feature sets the precision along the elongated axis 190, whereas the gripping element that is inserted into the slot retains an angle of the surgically implantable spacer 100. The gripping features that are formed extending partially through the material of the primary body side panel 112 avoids unwanted material from passing through the primary body side panel 112, where the material may interfere with movement or operation of the normal positioning member 140 and/or the translative positioning and locking control member 160. This can include the gripping element accidentally interfering with movement or operation of the normal positioning member 140 and/or the translative positioning and locking control member 160. The gripping features that are formed extending through the material of the primary body side panel 112 increases a surface area for grip between the gripping element and the gripping feature 122, 123. An edge of the gripping feature 122, 123 can be rounded, tapered, chamfered, squared, or of any other suitable shape.

The primary body 110 can include a series of retention features 128. In the exemplary illustration, the retention features 128 are formed in a shape of a linear ridge. Each exemplary ridge 128 is oriented extending between the first primary body side panel 112 and the second primary body side panel 112, preferably being substantially perpendicular to a plane defined by an interior surface of the first primary body side panel 112 and the second primary body side panel 112 or in a direction that is parallel to the 192. Each exemplary ridge 128 is shown being formed having a leading edge and a trailing edge. The leading edge has an angle extending away from the exterior surface of the bottom structure and towards the insertion end thereof. This angle assists during an insertion of the surgically implantable spacer 100 into the joint, where each ridge 128 would not hinder the insertion process. A trailing edge of each ridge 128 can be of any suitable shape, including an angle, rounded, and the like. In the exemplary illustration, the trailing edge is formed having an angle extending away from the exterior surface of the bottom structure and towards the insertion end thereof. This angle hinders or resists any motion of the surgically implantable spacer 100 in a direction opposite of the insertion direction. Gaps, grooves, slots, or any other formation can be provided between adjacent ridges 128, as shown in the figures. The gaps, grooves, slots, or any other formation provided between adjacent ridges 128 preferably passes through the 113. This reduces an overall weight of the surgically implantable spacer 100 and enables bone grafts to be packed into the interior of the surgically implantable spacer 100 and bone to grow around each ridge 128 and into the interior of the surgically implantable spacer 100.

Multiple series of translative positioning notches 126, 127 are included within the interior of the primary body 110. The series of translative positioning notches 126, 127 can extend upward from the interior surface of the 113, extend outward from the interior surface of the respective primary body side panel 112, or be formed as any other supporting structure within the primary body 110, or any combination thereof.

Details of features of each translative positioning notch 126, 127 are best presented in the illustration shown in FIG.

6 (using the primary body distal translative positioning notch 127 as an example for each translative positioning notch 126, 127). Each translative positioning notch 126, 127 includes a translative positioning notch seating section 132 for receiving and supporting a translative positioning and locking control member notch engaging projection 176 of the translative positioning and locking control member 160, a translative positioning notch retention section 134 for retaining the translative positioning and locking control member notch engaging projection 176 in a seated position within the translative positioning notch 126, and a translative positioning notch rising section 130 for transferring the translative positioning and locking control member notch engaging projection 176 from the current translative positioning notch seating section 132 to a translative positioning notch seating section 132 of an adjacent, higher translative positioning notch 126, 127. In the illustrated exemplary embodiment, the translative positioning notch 126, 127 is formed having a continuous arched surface. It is understood that the translative positioning notch 126, 127 can be formed having any suitable shape, including one having linear segments, different arched segments, any combination thereof, or any other suitable shape or combination of shapes. A transition between adjacent translative positioning notches 126, 127 can be rounded, chamfered, a sharp corner, or any other suitable transitional shape. Edges between each translative positioning notch 126, 127 and the interior surface of the respective primary body side panel 112 can include a fillet for reinforcement.

Figure 6:
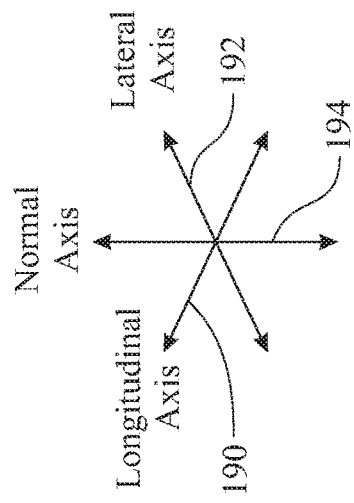
FIG. 6 presents an isometric enlarged view of the primary body detailing and identifying features of the translative positioning notch.
Figure 6:
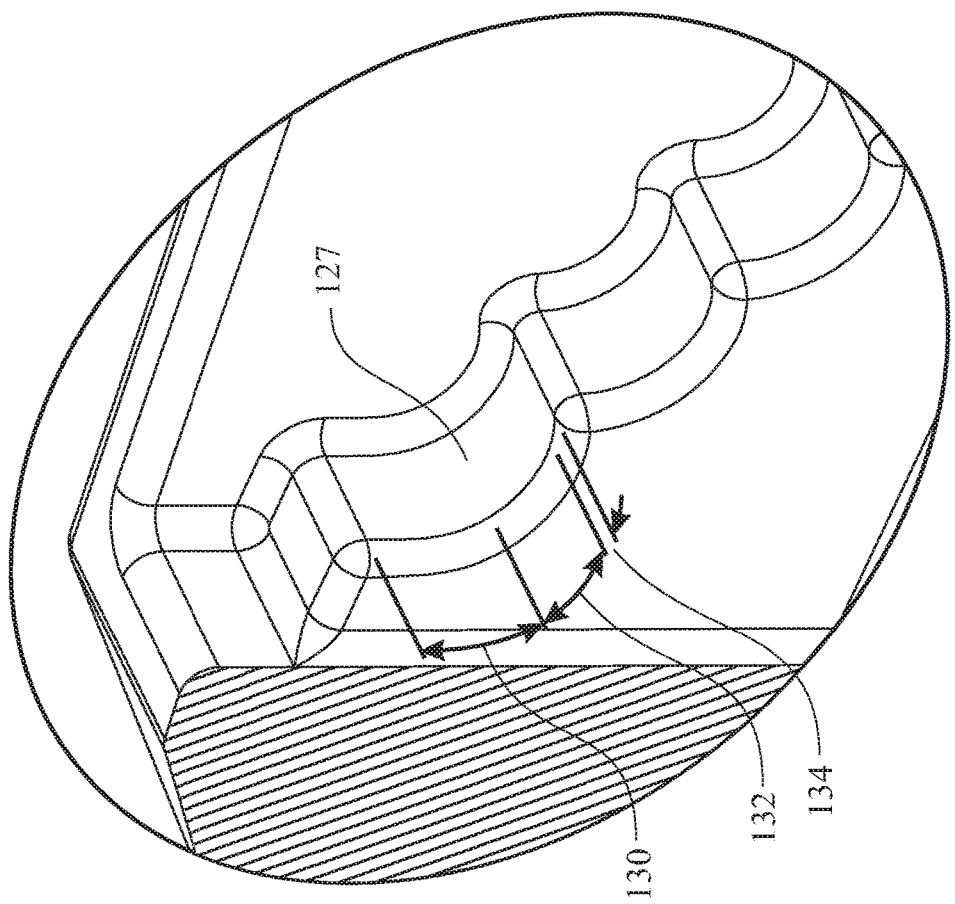
Figure 7:
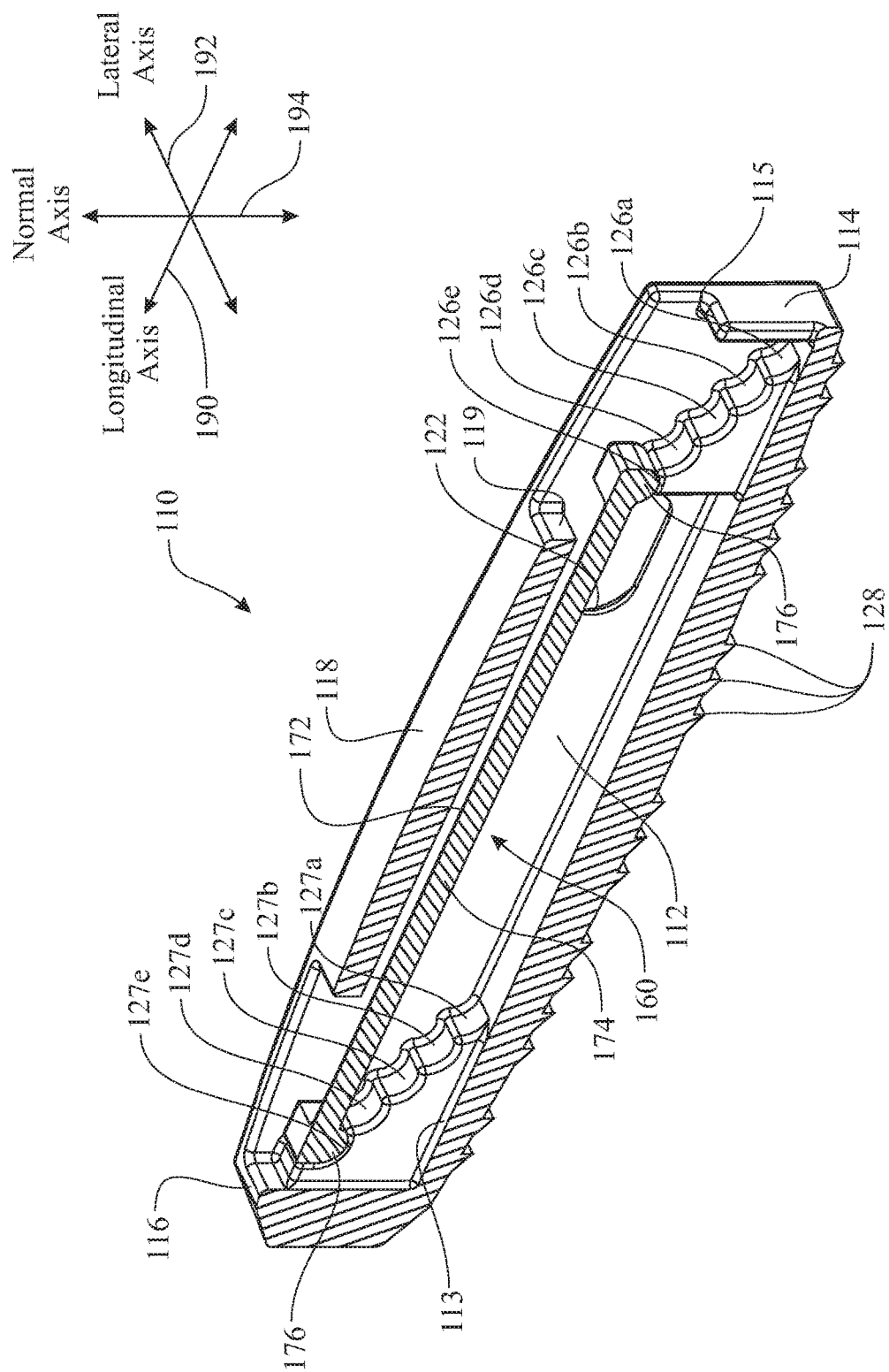
FIG. 7 presents an isometric cross section assembly view of the surgically implantable spacer replicating the view illustrated in FIG. 5, the surgically implantable spacer being shown in an assembled configuration illustrating the translative positioning and locking control member at a location which would position the normal positioning member in a spaced configuration, in this configuration each notch engaging projection is seated within a raised respective primary body translative positioning notch, the section being taken along section line 5-5 of FIG. 1.
Figure 8:
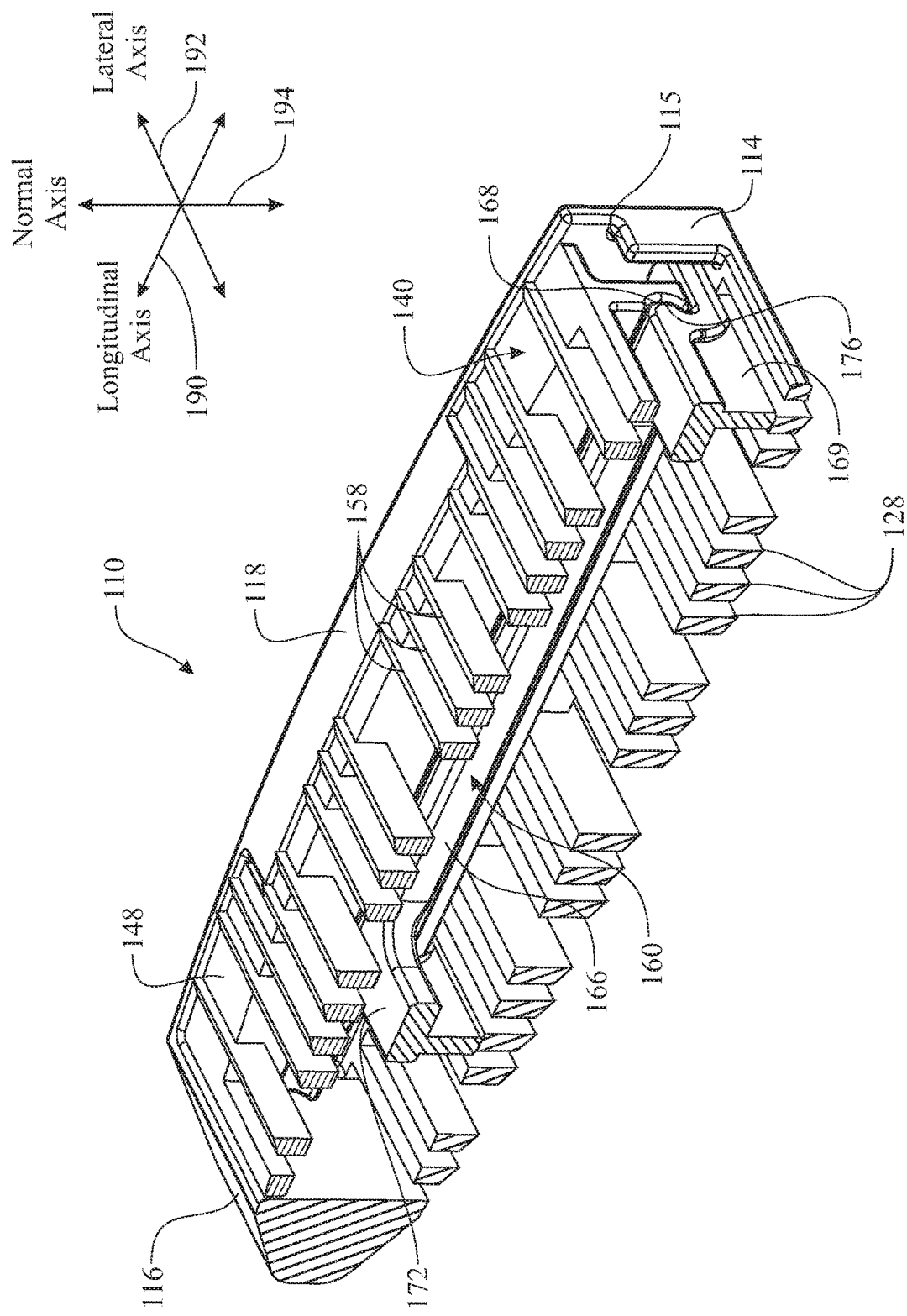
FIG. 8 presents an isometric cross section assembly view of the surgically implantable spacer originally introduced in FIG. 1, the surgically implantable spacer being shown in an assembled configuration illustrating an interaction between the normal positioning member and the translative positioning and locking control member, the assembly shown in an insertion configuration, the section being taken along section line 8-8 of FIG. 1.
Figure 9:
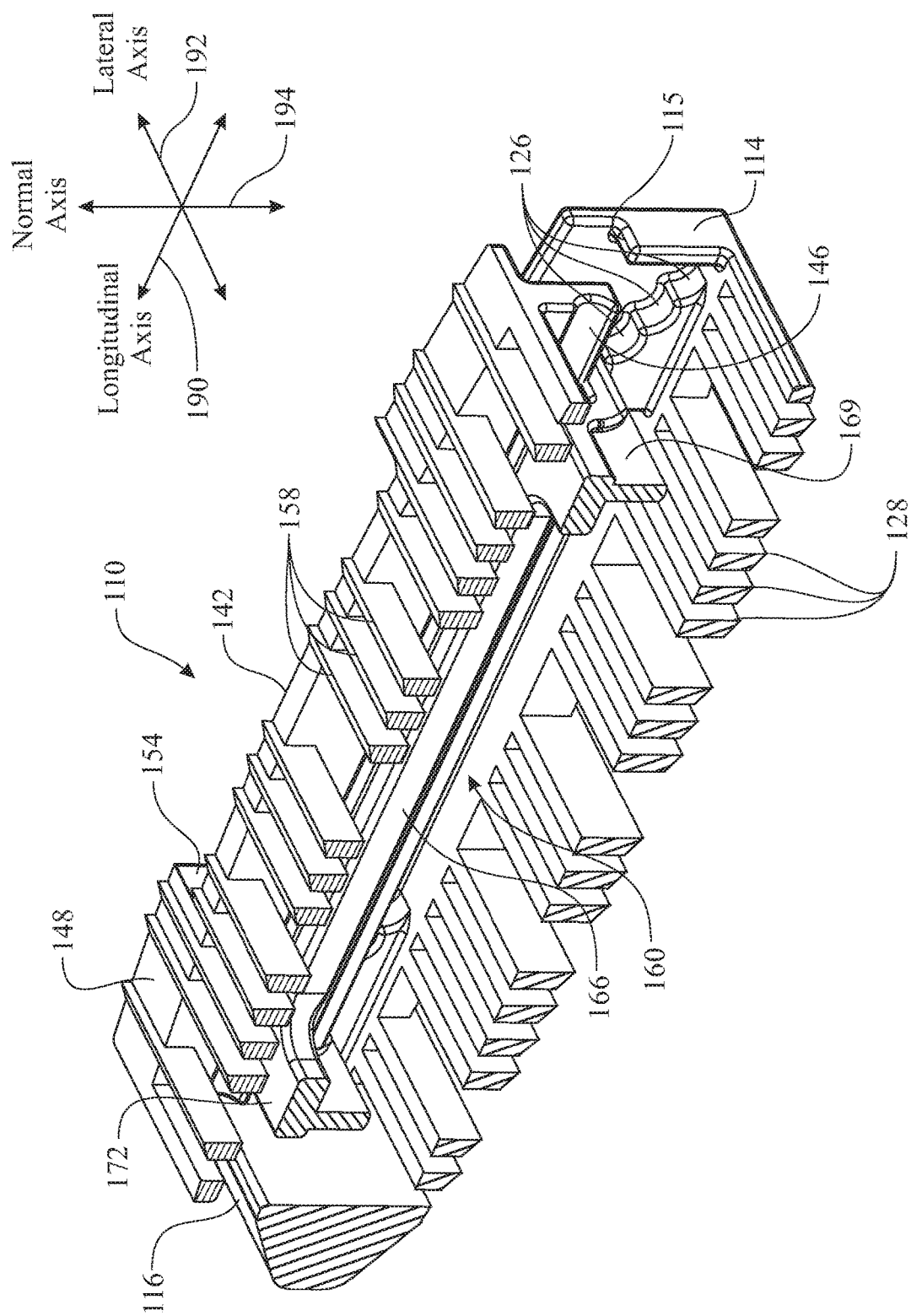
FIG. 9 presents an isometric cross section assembly view of the surgically implantable spacer replicating the view illustrated in FIG. 5, the surgically implantable spacer being shown in an assembled configuration illustrating the translative positioning and locking control member positioning the normal positioning member in a spaced configuration, the section being taken along section line 8-8 of FIG. 1.
Figure 10:
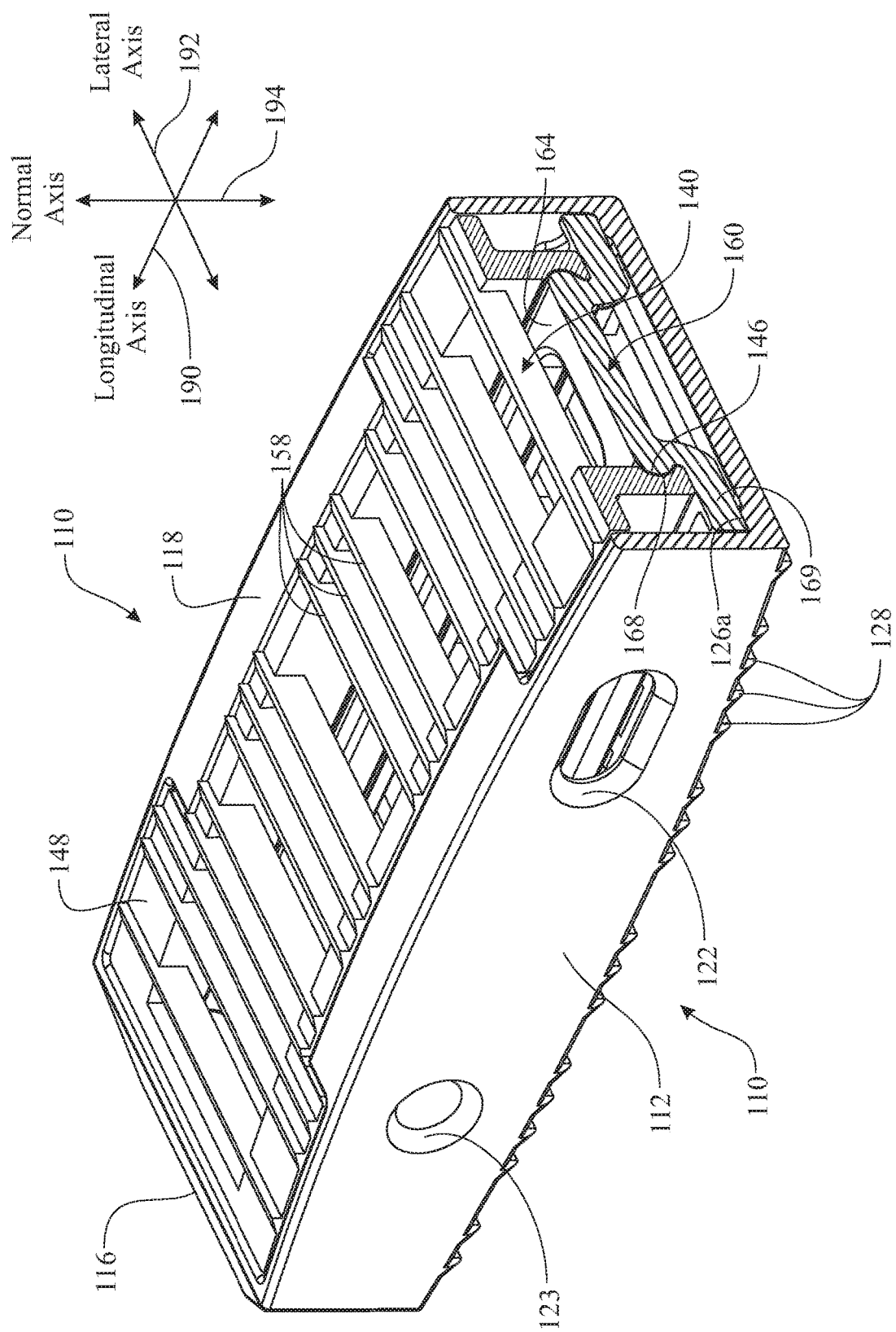
FIG. 10 presents an isometric cross section assembly view of the surgically implantable spacer originally introduced in FIG. 1, the surgically implantable spacer being shown in an assembled configuration illustrating an interaction between the normal positioning member and the translative positioning and locking control member, the assembly shown in an insertion configuration, the section being taken along section line 10-10 of FIG. 1.
Figure 11:
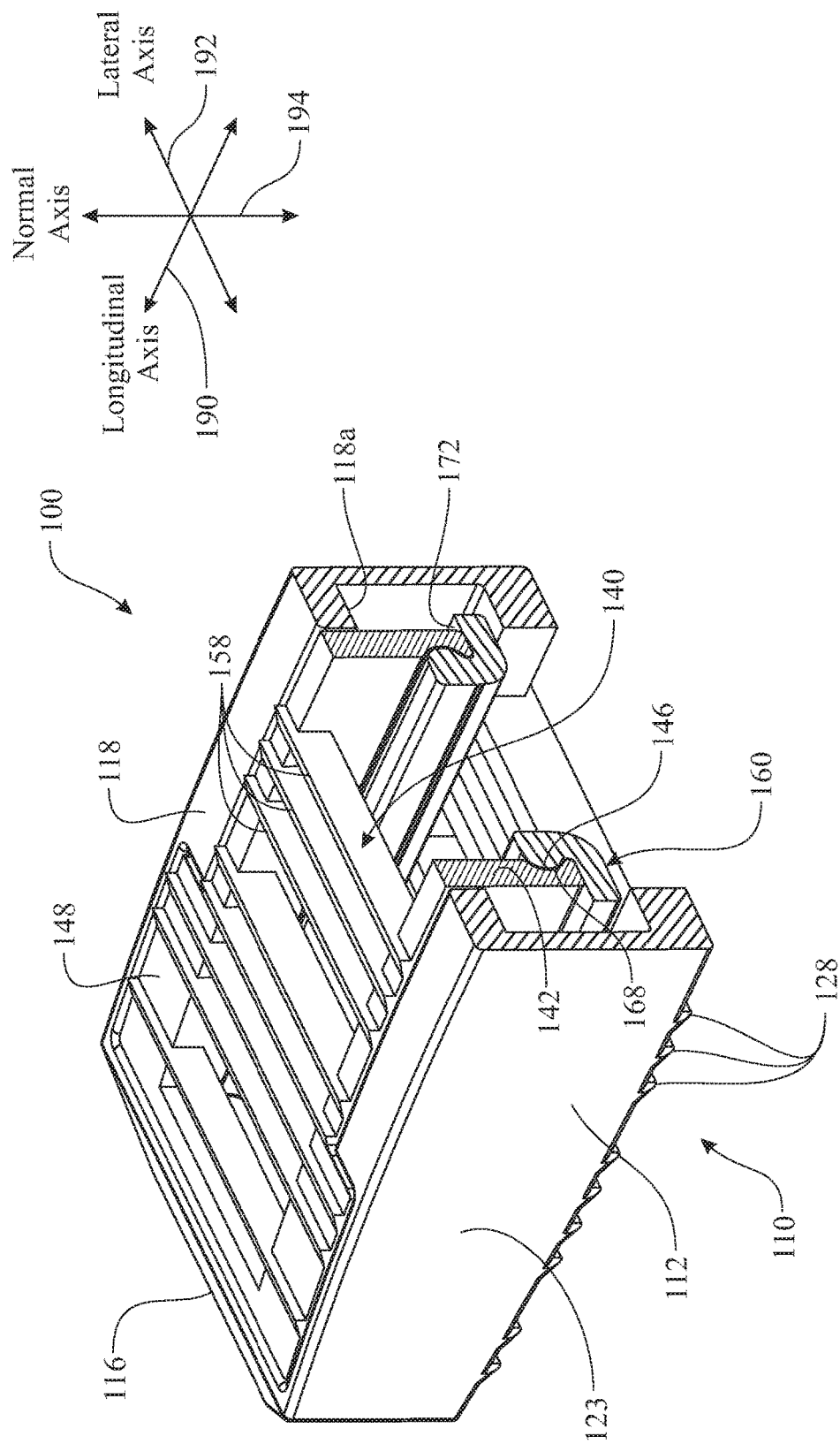
FIG. 11 presents an isometric cross section assembly view of the surgically implantable spacer originally introduced in FIG. 1, the surgically implantable spacer being shown in an assembled configuration illustrating an interaction between the normal positioning member and the translative positioning and locking control member, the assembly shown in an insertion configuration, the section being taken along section line 11-11 of FIG. 1.
Figure 12:
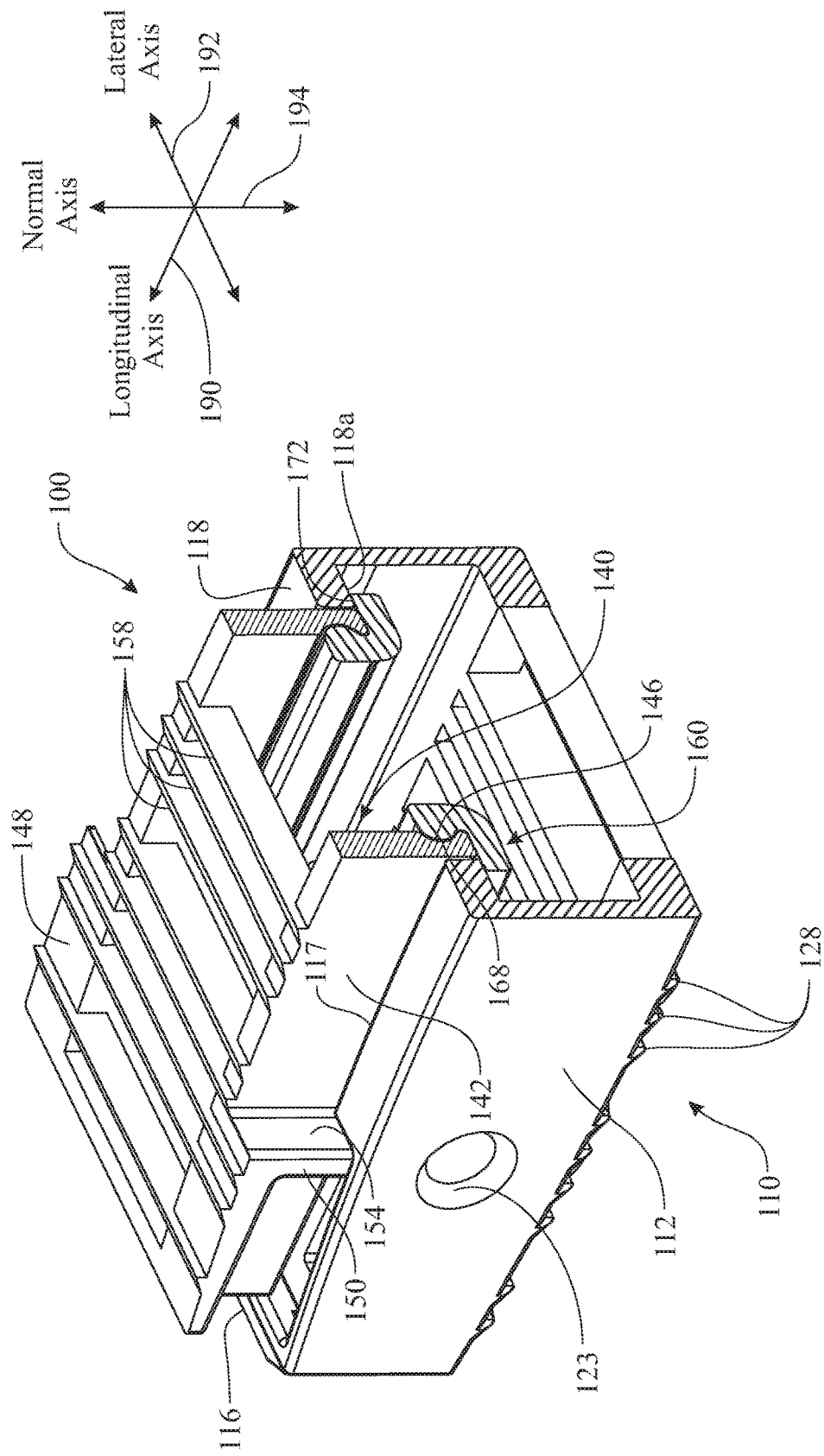
FIG. 12 presents an isometric cross section assembly view of the surgically implantable spacer originally introduced in FIG. 1, the surgically implantable spacer being shown in an assembled configuration illustrating an interaction between the normal positioning member and the translative positioning and locking control member, the assembly shown in a spaced configuration, the section being taken along section line 11-11 of FIG. 1.

In the exemplary illustration, the series of translative positioning notches 126, 127 are formed where a translative positioning notch 126a, 127a located proximate an insertion end of the series is closes to the interior surface of the primary body bottom structure 113, and each adjacent translative positioning notch 126b, 127b is formed slightly further from interior surface of the primary body bottom structure 113, thus creating a stair-step arrangement of the series of translative positioning notches 126, 127. In more detail of the series of translative positioning notches 126, as illustrated in FIG. 6, the 126a is located closest to the insertion end of the series and closest to the interior surface of the primary body bottom structure 113. The primary body proximal translative positioning notch 126b is located adjacent to the primary body proximal translative positioning notch 126a, on side closer to the primary body distal end panel 116; the primary body proximal translative positioning notch 126b being slightly further from the interior surface of the primary body bottom structure 113 compared to the primary body proximal translative positioning notch 126a.

The primary body proximal translative positioning notch 126c is located adjacent to the primary body proximal translative positioning notch 126b, on side closer to the primary body distal end panel 116; the primary body proximal translative positioning notch 126c being slightly further from the interior surface of the primary body bottom structure 113 compared to the primary body proximal translative positioning notch 126b.

The primary body proximal translative positioning notch 126d is located adjacent to the primary body proximal translative positioning notch 126c, on side closer to the primary body distal end panel 116; the primary body proximal translative positioning notch 126d being slightly further from the interior surface of the primary body bottom structure 113 compared to the primary body proximal translative positioning notch 126c.

The primary body proximal translative positioning notch 126e is located adjacent to the primary body proximal translative positioning notch 126d, on side closer to the primary body distal end panel 116; the primary body proximal translative positioning notch 126e being slightly further from the interior surface of the primary body bottom structure 113 compared to the primary body proximal translative positioning notch 126d.

The exemplary series of translative positioning notches 127 includes a primary body distal translative positioning notch 127a, a primary body distal translative positioning notch 127b, a primary body distal translative positioning notch 127c, a primary body distal translative positioning notch 127d, and a primary body distal translative positioning notch 127e, where the arrangement of the primary body distal translative positioning notches 127a, 127b, 127c, 127d, 127e mimic the arrangement of the primary body proximal translative positioning notched 126a, 126b, 126c, 126d, 126e.

The primary body 110 can further comprise a normal retention feature 118. In the exemplary illustration, the normal retention feature 118 is provided in a form of a flange. The primary body top flange 118 extends from the interior surface of the respective primary body side panel 112 at a location proximate an upper edge. The primary body top flange 118 extends between a primary body top flange lateral edge 119 located closer to the distal end of the primary body 110 and a second primary body top flange lateral edge 119 located closer to the insertion end of the primary body 110. The primary body top flange 118 includes an interior edge defined as a primary body top flange interior edge 117. The primary body top flange interior edge 117 is preferably oriented being substantially parallel to a plane defined by the elongated axis 190 and the normal axis 194. Each primary body top flange lateral edge 119 is preferably oriented being substantially parallel to a plane defined by the lateral axis 192 and the normal axis 194. The primary body top flange 118 additionally is defined by a thickness or a dimension of the material measured along the normal axis 194 axis. The thickness extends between an exterior surface of the primary body top flange 118 and a primary body top flange interior normal motion limiting surface 118a.

Primary body insertion end flanges 114 of a pair of primary body insertion end flanges 114 are located at an insertion end of the primary body 110. The primary body insertion end flange 114 extends between the interior surface of the primary body bottom structure 113 and a primary body insertion end flange assembly clearance notch 115, where the primary body insertion end flange assembly clearance notch 115 is located at a distance from the upper or top edge of the primary body side panel 112. The primary body insertion end flange 114 is oriented to be generally parallel to a plane defined by the lateral axis 192 and the normal axis 194. The primary body insertion end flange assembly clearance notch 115 is preferably generally parallel to a plane defined by the lateral axis 192 and the elongated axis 190. An interior surface of the primary body insertion end flange 114 is located providing sufficient clearance to enable the translative positioning and locking control member notch engaging projection 176 to seat onto the respective primary body proximal translative positioning notch 126a. The primary body insertion end flange assembly clearance notch 115 is at a sufficient distance from the primary body top flange interior normal motion limiting surface 118a to create a gap enabling the translative positioning and locking control member notch engaging projection 176 to pass therebetween.

The normal positioning member 140 includes a normal positioning member top structure 148, wherein an exterior surface of the normal positioning member top structure 148 is preferably sized and shaped to follow a contour of the upper edge of each primary body side panel 112. A peripheral edge of the normal positioning member top structure 148 preferably follows a contour of an opening defined by the interior surface of each primary body side panel 112, the interior surface of the primary body distal end panel 116, each of the distal primary body top flange lateral edges 119 of the respective primary body top flange 118, each primary body top flange interior edge 117 of the respective primary body top flange 118, and each of the proximal or insertion end primary body top flange lateral edge 119. An edge of the normal positioning member top structure 148 located proximate the insertion end of the primary body 110 is preferably sized and shaped to follow a contour of an interior surface of each primary body insertion end flange 114.

The normal positioning member 140 includes a pair of normal positioning member side panel 142. Each normal positioning member side panel 142 has a length extending between a first normal positioning member side panel end surface 144 and a second normal positioning member side panel end surface 144.

Each normal positioning member side panel 142 extends generally perpendicularly to the normal positioning member top structure 148, wherein each normal positioning member side panel 142 is oriented being substantially parallel to a plane defined by the elongated axis 190 and the normal axis 194. The normal positioning member side panels 142 of the pair of normal positioning member side panels 142 are spaced apart at a distance where the exterior surface of the normal positioning member side panel 142 fit between exposed or interior surfaces of opposing series of translative positioning notches 126, 127. Coincidentally, the primary body top flange interior edge 117 is located on a plane that is substantially close to and preferably overlapping a plane defined by an interior surface of the interior surfaces of opposing series of translative positioning notches 126, 127.

A normal positioning member elongated formation 146 is formed on an interior surface of each normal positioning member side panel 142, the normal positioning member elongated formation 146 extending in a direction parallel to the elongated axis 190. The normal positioning member elongated formation 146 can be provided in any suitable formation. In the exemplary illustration, the normal positioning member elongated formation 146 is provided as a groove. It is understood that the normal positioning member elongated formation 146 can be provided as an elongated projection or a tail.

The normal positioning member 140 preferably includes a normal translation guide feature. In the exemplary illustrations, the normal translation guide feature is sized and shaped to slideably engage with the primary body top flange 118. The exemplary normal translation guide feature of the normal positioning member 140 includes the normal positioning member side panel 142 and a pair of normal positioning member guide feature guide surfaces 154, wherein each normal positioning member guide feature guide surface 154 is provided by a normal positioning member guide feature 150. Each normal positioning member guide feature guide surface 154 is located, sized, and shaped to slideably engage with the respective mating primary body top flange lateral edge 119. It is preferred that each normal positioning member guide feature guide surface 154 is oriented to be parallel with a plane defined by the normal axis 194 and the lateral axis 192. It is understood that the surface of each normal positioning member guide feature guide surface 154 can vary from the illustrated exemplary embodiment. The varied angles of each normal positioning member guide feature guide surface 154 can provide different functions. For example, it is understood that the surface of each normal positioning member guide feature guide surface 154 can be oriented by rotating the surface about the normal axis 194. In one arrangement, the surface of each of the distal normal positioning member guide feature guide surface 154 and the insertion normal positioning member guide feature guide surface 154 can be arranged to create a dovetail shape, where the free or distal edges of the normal positioning member guide feature guide surface 154 are closer to one another when compared to the connected edges of the normal positioning member guide feature guide surface 154. The dovetailed arrangement can retain a width between the pair of primary body side panels 112, wherein the dovetailed arrangement draws each primary body side panel 112 inward, towards one another.

In another arrangement, each normal positioning member guide feature guide surface 154 can be oriented where the surface is rotated about the lateral axis 192. This arrangement would slide the normal positioning member 140 along a path that is offset from the normal axis 194.

The normal positioning member top structure 148 can be formed having an exterior surface that is of any suitable shape. IN the exemplary illustration, the exterior surface of the normal positioning member top structure 148 is provided having an arched shape, more specifically, a convex arched shape. Although the exemplary exterior surface is illustrated having the convex arched shape, it is understood that the exterior surface can be of any suitable shape, including a planar shape, a complex arched shape, a concave arched shape, and the like.

The normal positioning member top structure 148 can include a plurality of normal positioning member retention features 158. The normal positioning member retention features 158 can be similar to the primary body retention features 128 previously described. The normal positioning member top structure 148 can be formed having a series of gaps or passageways passing therethrough, similar to those described in the primary body bottom structure 113. The series of retention features 158 of the normal positioning member top structure 148 can mimic the series of retention features 128 of the primary body bottom structure 113. The series of retention features 158 of the normal positioning member top structure 148 can mirror the series of retention features 128 of the primary body bottom structure 113. The series of retention features 158 of the normal positioning member top structure 148 can differ from the series of retention features 128 of the primary body bottom structure 113. The series of retention features 158 of the normal positioning member top structure 148 can differ significantly in at least one of size, shape, arrangement, and the like from the series of retention features 128 of the primary body bottom structure 113.

The translative positioning and locking control member 160 is formed of any suitable shape comprising two key features: (a) a normal positioning member mating elongated formation 168 and a plurality of translative positioning and locking control member notch engaging projections 176. As illustrated in the exemplary embodiment, it is preferred that the normal positioning member mating elongated formation 168 is on a plane above a plane defined by the plurality of translative positioning and locking control member notch engaging projections 176. The plurality of translative positioning and locking control member notch engaging projections 176 extend outward from a base portion of a body of the translative positioning and locking control member 160.

The plurality of translative positioning and locking control member notch engaging projections 176 preferably define a plane that is substantially parallel to a plane defined by the elongated axis 190 and the lateral axis 192. It is preferable that contacting surfaces of the translative positioning and locking control member notch engaging projection 176 are along the same plane. A normally translative limiting feature of the translative positioning and locking control member 160 extends outward as a portion of the base portion of the body of the translative positioning and locking control member 160, wherein the normally translative limiting feature extends between interior edges or facing edges of pairs of adjacently arranged translative positioning and locking control member notch engaging projections 176. The normally translative limiting feature includes a translative positioning and locking control member base flange top surface 172, wherein the translative positioning and locking control member base flange top surface 172 is oriented being substantially parallel to a plane defined by the elongated axis 190 and the lateral axis 192. The normally translative limiting feature extends outward, terminating at a translative positioning and locking control member base flange exterior surface 174, wherein the translative positioning and locking control member base flange exterior surface 174 is oriented being substantially parallel to a plane defined by the elongated axis 190 and the normal axis 194. Each normal positioning member mating elongated formation 168 is formed along each edge of a translative positioning and locking control member top section 164. The translative positioning and locking control member top section 164 is formed above the base portion of a body of the translative positioning and locking control member 160. Each normal positioning member mating elongated formation 168 can be formed as a projection (as shown in the exemplary illustrations), a groove (similar to the normal positioning member elongated axial groove 146), or any other shape to mate with the normal positioning member elongated formation 146. In another example, the normal positioning member mating elongated formation 168 can be provided in a form of a tongue and the normal positioning member elongated formation 146 can be provide in a form of a groove. In yet another example, the normal positioning member mating elongated formation 168 can be provided in a form of a groove and the normal positioning member elongated formation 146 can be provide in a form of a tongue. In yet another example, the normal positioning member mating elongated formation 168 can be provided in a form of a tail and the normal positioning member elongated formation 146 can be provide in a form of a dovetail groove.

A translative positioning and locking control member elongated axis beltline 170 can be formed between the translative positioning and locking control member top section 164 and the base portion of a body of the translative positioning and locking control member 160. A translative positioning and locking control member end panel 169 can be included at each of a distal end of the translative positioning and locking control member 160 and an insertion or proximal end of the translative positioning and locking control member 160. The translative positioning and locking control member end panel 169 provides mechanical or structural support between each of a pair of translative positioning and locking control member notch engaging projection 176 that extend outward in opposite directions.

A translative positioning and locking control member top section interior cutout 166 can be formed through the translative positioning and locking control member top section 164. The translative positioning and locking control member top section interior cutout 166 reduces material and weight of the translative positioning and locking control member 160, and thus the same of the surgically implantable spacer 100. The corners and edges of the translative positioning and locking control member top section interior cutout 166 are preferably chamfered or rounded to reduce stress concentrations within the translative positioning and locking control member 160.

Figure 16:
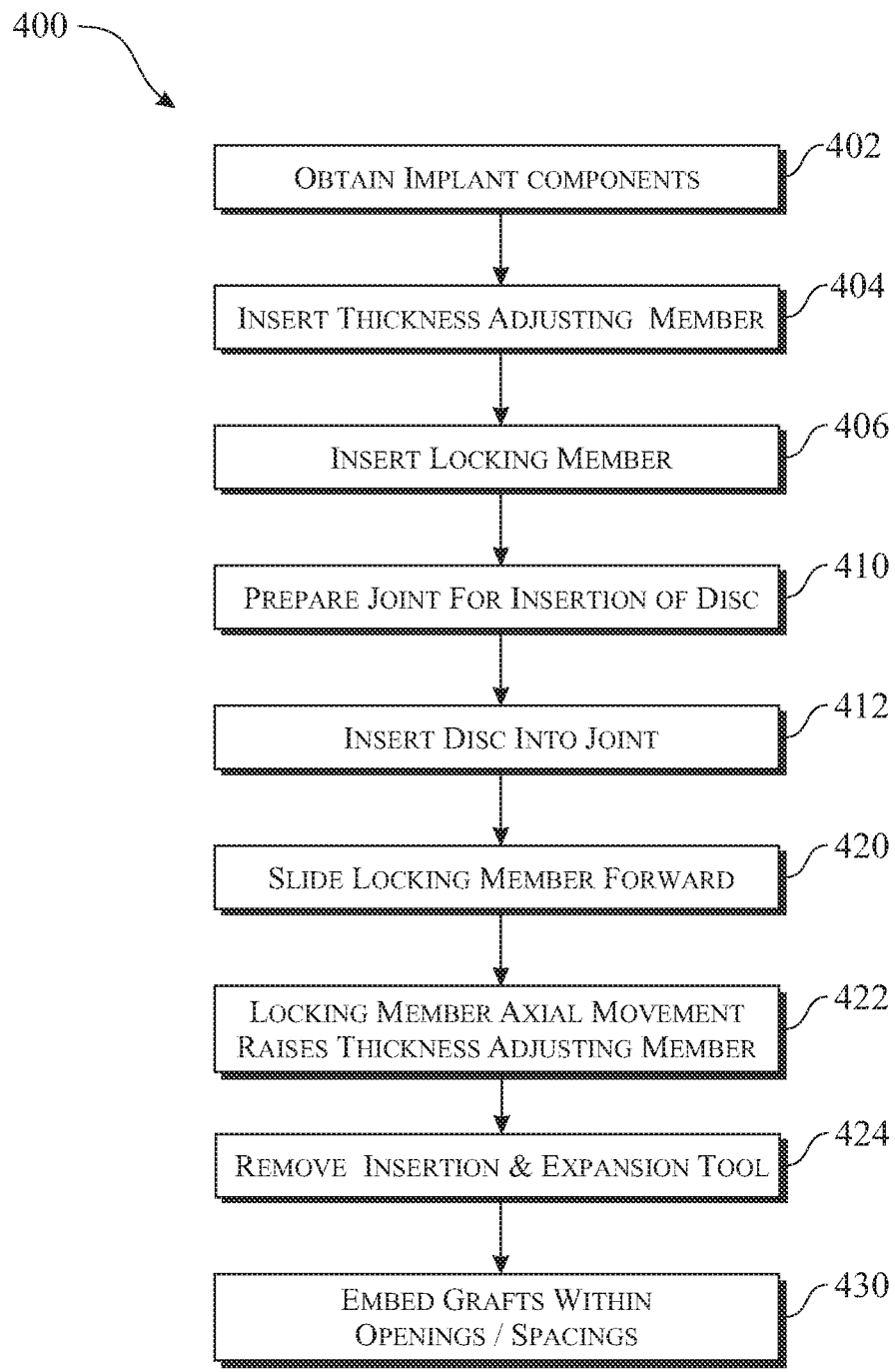
FIG. 16 presents an exemplary flow diagram describing a method of using the surgically implantable spacer.

A method of assembling and operating the surgically implantable spacer 100 is illustrated in FIGS. 2 through 12, with FIG. 16 presenting a replacement spacer assembly and insertion process flow diagram 400 detailing the process. The a replacement spacer assembly and insertion process flow diagram 400 initiates with a step of obtaining the components of the surgically implantable spacer 100, including the primary body 110, the normal positioning member 140, and the translative positioning and locking control member 160 (step 402). The normal positioning member 140 is slideably assembled to the primary body 110 in a direction of the normal axis 194 (step 404). The normal positioning member side panel 142 is located to slide against the respective primary body top flange interior edge 117. Each normal positioning member guide feature guide surface 154 is located to slide against the respective primary body top flange lateral edge 119.

Figure 2:
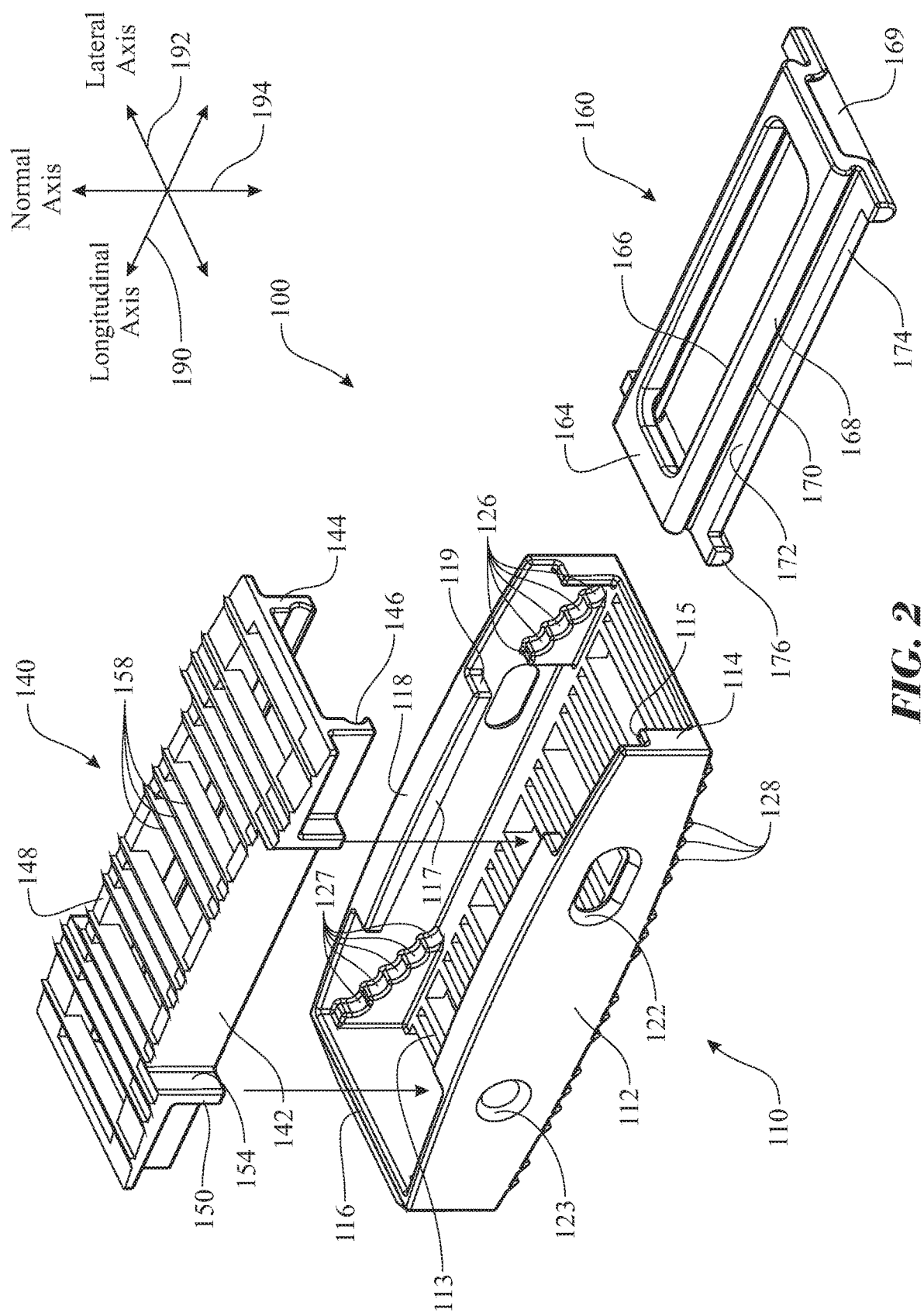
FIG. 2 presents an isometric top, side exploded assembly view of the surgically implantable spacer originally introduced in FIG. 1, the surgically implantable spacer being shown in a disassembled or preassembly configuration.
Figure 3:
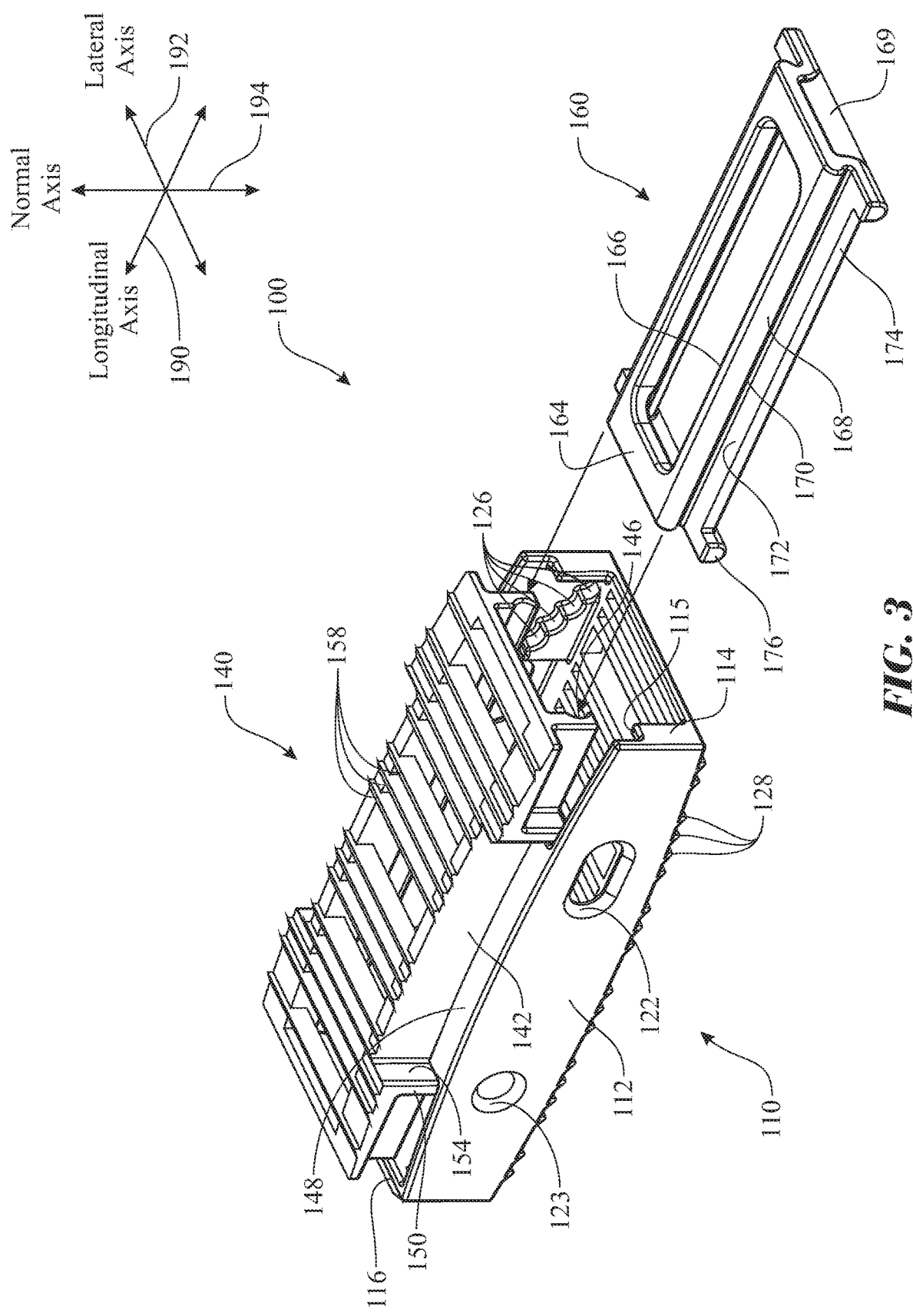
FIG. 3 presents an isometric top, side exploded assembly view of the surgically implantable spacer originally introduced in FIG. 1, the surgically implantable spacer being shown in a partially assembled configuration illustrating an assembly step of slideably assembling the normal positioning member and the primary body to one another.
Figure 4:
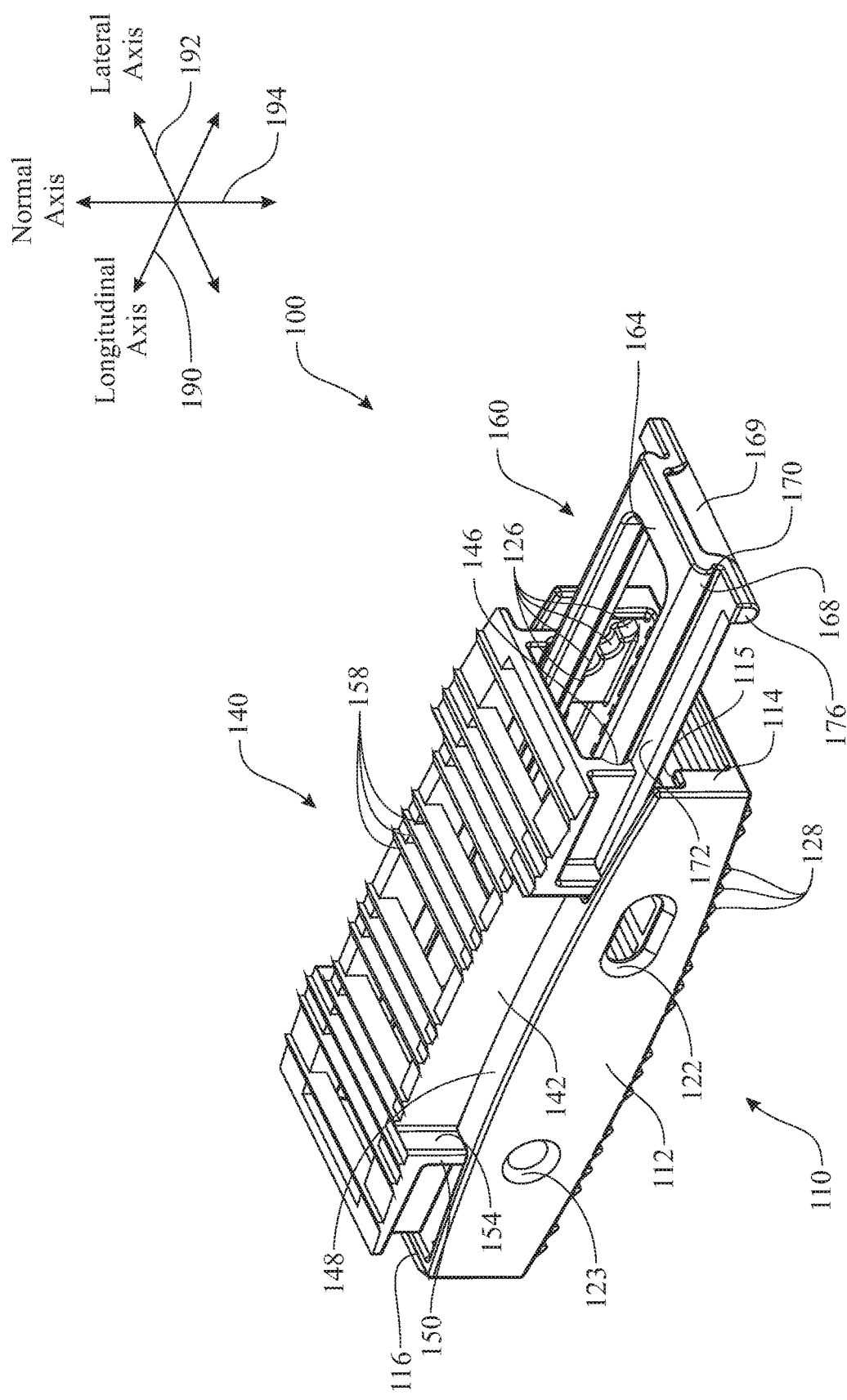
FIG. 4 presents an isometric top, side exploded assembly view of the surgically implantable spacer originally introduced in FIG. 1, the surgically implantable spacer being shown in a partially assembled configuration illustrating an assembly step of slideably assembling the translative positioning and locking control member and the normal positioning member to one another.

The normal positioning member 140 is slideably inserted into the primary body 110, as shown in FIG. 2, positioning the normal positioning member elongated axial groove 146 at a location that is approximately in alignment with the primary body top flange interior edge 117, as shown in FIG. 3. The translative positioning and locking control member 160 is inserted into the primary body 110, as shown in FIG. 4, passing the distal or leading edge translative positioning and locking control member notch engaging projections 176 above the primary body insertion end flange assembly clearance notch 115 (step 406). During the insertion of the translative positioning and locking control member 160 into the primary body 110, each translative positioning and locking control member top section elongated side edge 168 is slideably engaging with each respective normal positioning member elongated axial groove 146.

Figure 5:
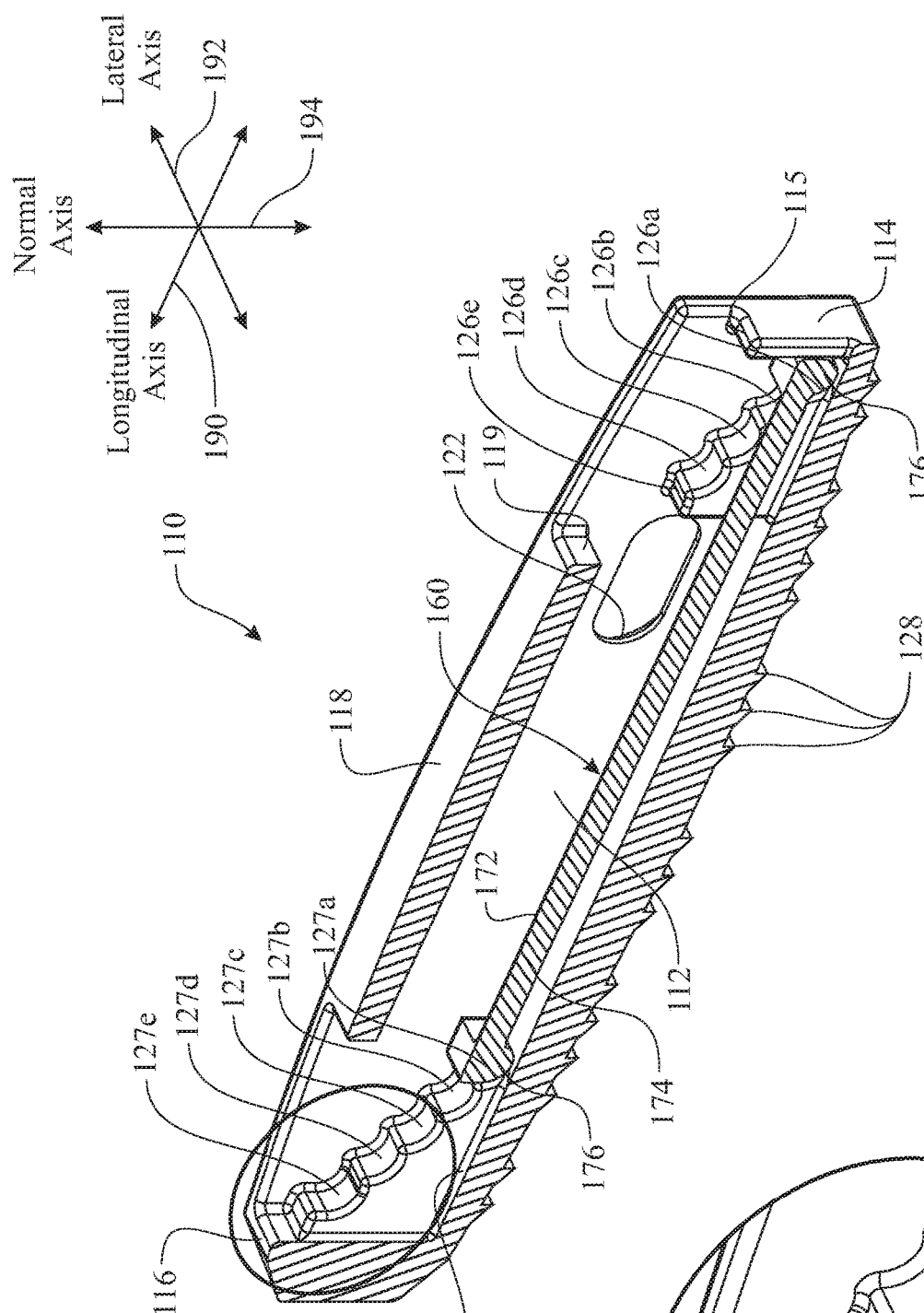
FIG. 5 presents an isometric cross section assembly view of the surgically implantable spacer originally introduced in FIG. 1, the surgically implantable spacer being shown in an assembled configuration illustrating the translative positioning and locking control member in an insertion configuration, in this configuration each notch engaging projection is seated within a lowest respective primary body translative positioning notch, the section being taken along section line 5-5 of FIG. 1.

Once the trailing pair of translative positioning and locking control member notch engaging projections 176 pass across the primary body insertion end flange assembly clearance notch 115, the combination of the normal positioning member 140 and translative positioning and locking control member 160, a compression force can be applied to the exterior surface of the normal positioning member top structure 148, driving the combination of the normal positioning member 140 and translative positioning and locking control member 160 towards the interior surface of the primary body bottom structure 113. Each of the series of translative positioning and locking control member notch engaging projections 176 are seated into the translative positioning notch seating section 132 of the respective primary body proximal translative positioning notch 126a, 127a, as illustrated in FIG. 5. This places the surgically implantable spacer 100 in an insertion configuration, as illustrated in FIGS. 1, 5, 8, and 10.

Figure 13:
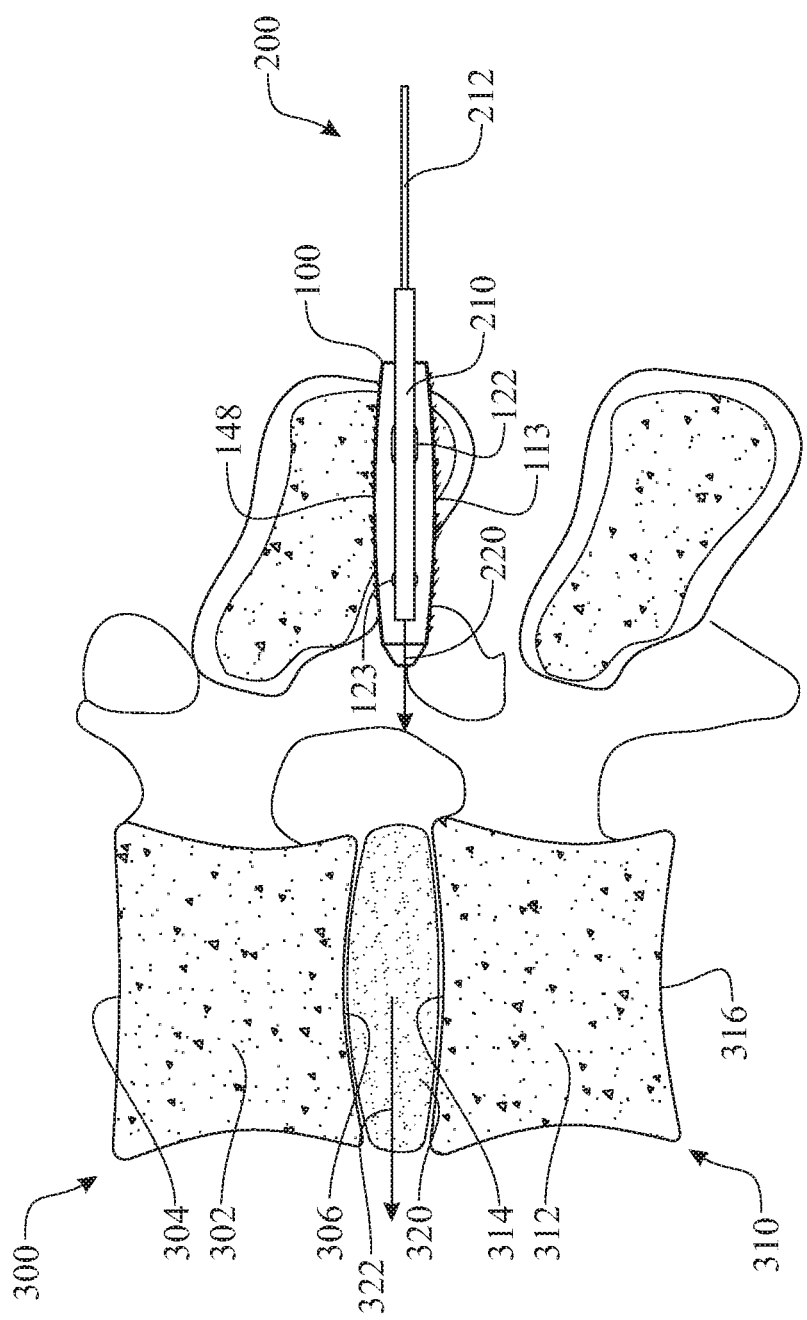
FIG. 13 presents an sectioned elevation view of the surgically implantable spacer shown in an exemplary biological application, wherein the surgically implantable spacer is shown being inserted between two adjacent vertebrae.

The surgically implantable spacer 100 is implanted within a joint of a patient. In the exemplary embodiment, illustrated in FIGS. 13, 14 and 15, the exemplary joint is between a first joint member 300 and a second joint member 310. The first vertebrae 302 includes a first vertebrae first joint surface 304 on a first side and a first vertebrae second joint surface 306 on a second, opposite side. Similarly, the second vertebrae 312 includes a second vertebrae second joint surface 314 on a first side and a second vertebrae second joint surface 316 on a second, opposite side. More specifically, the joint is formed between the first vertebrae second joint surface 306 of the first vertebrae 302 and the second vertebrae second joint surface 314 of the second vertebrae 312. In the exemplary embodiment, the joint is prepared for insertion of the surgically implantable spacer 100 by removing a intravertebral disc 320 from between the first vertebrae second joint surface 306 of the first vertebrae 302 and the second vertebrae second joint surface 314 of the second vertebrae 312, in accordance with a intra-vertebral disc removal 322 (step 410), and replaced with the surgically implantable spacer 100.

The collapsed surgically implantable spacer 100 is retained by a spacer insertion and expansion control mechanism assembly 200. The spacer insertion and expansion control mechanism assembly 200 includes a plurality of gripping elements (not shown but well understood by description); wherein the gripping elements are supported by a spacer insertion and spacing control handle 210. The gripping elements of the spacer insertion and expansion control mechanism assembly 200 are arranged on the spacer insertion and expansion control mechanism assembly 200 to engage with gripping features 122, 123 of the surgically implantable spacer 100. A spacer insertion and spacing translative positioning element 212 is slideably assembled to the spacer insertion and spacing control handle 210. The spacer insertion and spacing translative positioning element 212 is designed to engage with at least one feature of the translative positioning and locking control member 160, wherein the at least one feature is preferably located at a proximal or insertion end of the translative positioning and locking control member 160. In one application, the spacer insertion and spacing translative positioning element 212 would be designed to engage with the translative positioning and locking control member end panel 169. In another application, the spacer insertion and spacing translative positioning element 212 would be designed to engage with a proximal edge of the translative positioning and locking control member top section 164.

Figure 14:
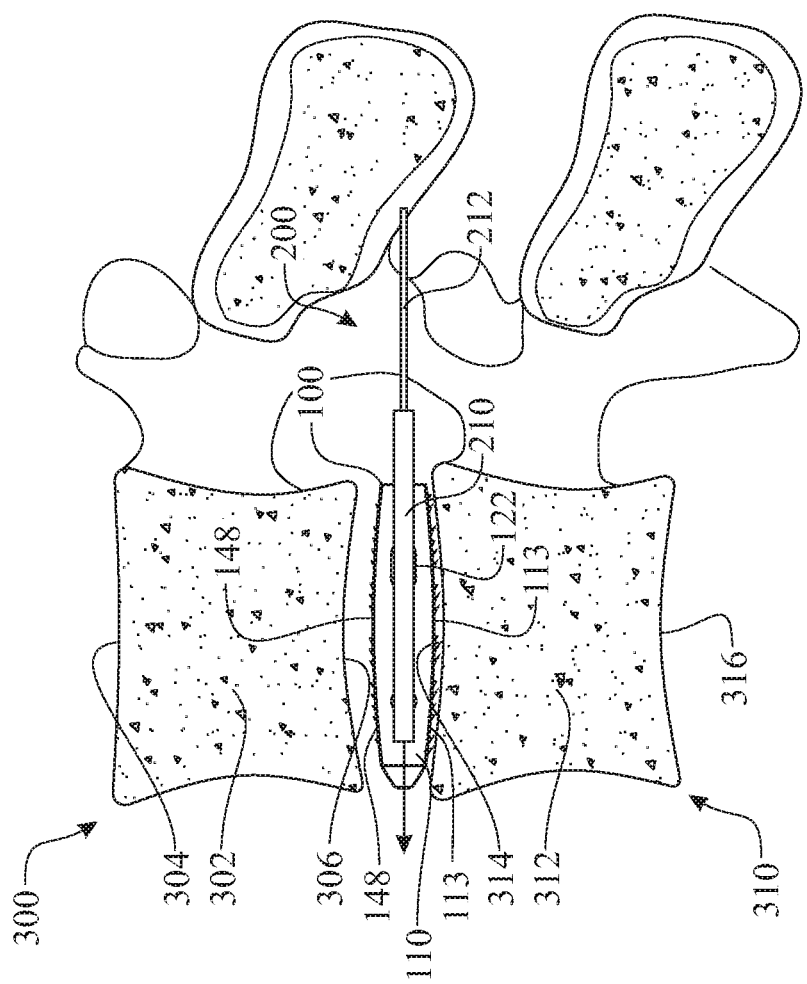
FIG. 14 presents an sectioned elevation view of the surgically implantable spacer shown in the exemplary biological application, wherein the surgically implantable spacer remains in an insertion configuration and is inserted in position between two adjacent vertebrae.
Figure 15:
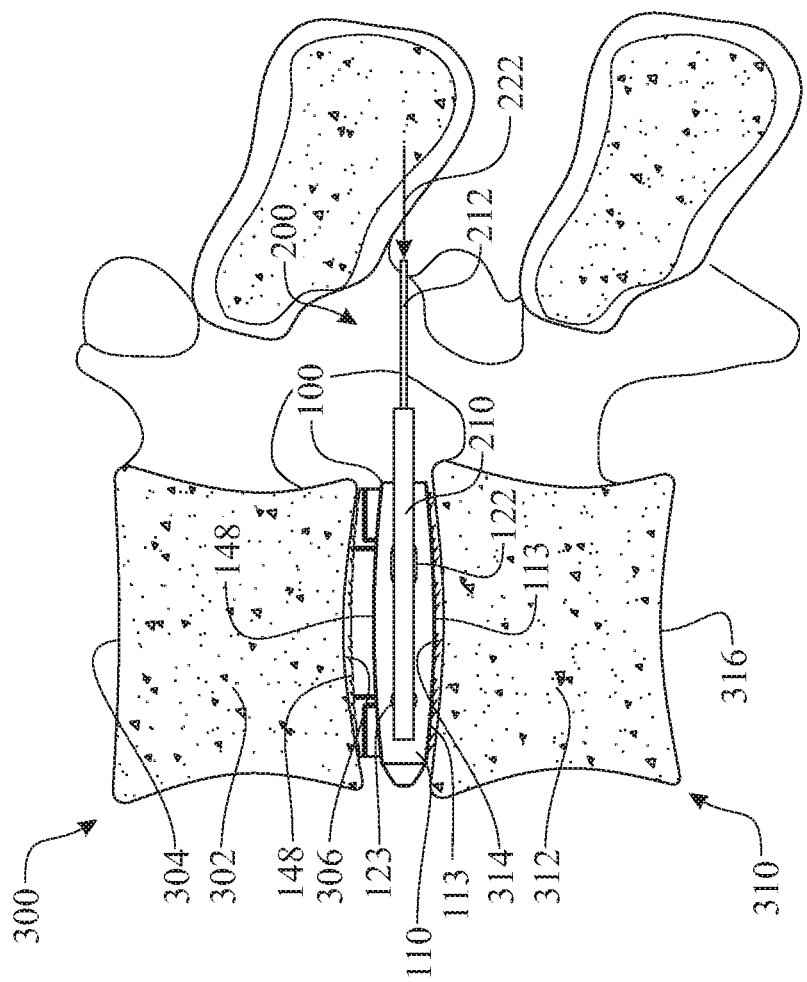
FIG. 15 presents an sectioned elevation view of the surgically implantable spacer shown in the exemplary biological application, wherein the surgically implantable spacer is manipulated into a spaced configuration in position between two adjacent vertebrae.

The surgeon would utilize the spacer insertion and expansion control mechanism assembly 200 to manipulate and maneuver 220 the surgically implantable spacer 100 into a position between the first vertebrae second joint surface 306 of the first vertebrae 302 and the second vertebrae second joint surface 314 of the second vertebrae 312, as illustrated in FIG. 14 (step 412). Once the surgically implantable spacer 100 is properly positioned, the surgeon would retain the spacer insertion and spacing control handle 210 in position and apply a spacer insertion and spacing translative force 222 to the spacer insertion and spacing translative positioning element 212, as illustrated in FIG. 15 (step 420). The spacer insertion and spacing control handle 210 supports the primary body 110, while the spacer insertion and spacing translative positioning element 212 drives the translative positioning and locking control member 160 towards the distal end of the primary body 110. As the translative positioning and locking control member 160 moves forward, each translative positioning and locking control member notch engaging projection 176 is driven upwards along a respective translative positioning notch rising section 130, until each translative positioning and locking control member notch engaging projection 176 becomes seated in the translative positioning notch seating section 132 of an adjacent primary body translative positioning notch 126, 127 (step 422). As the translative positioning and locking control member 160 is driven to each adjacent primary body translative positioning notch 126, 127, the translative positioning and locking control member 160 is driven further from the interior surface of the primary body bottom structure 113. The engagement between the translative positioning and locking control member top section elongated side edge 168 and the normal positioning member elongated axial groove 146, causes the normal positioning member 140 to separate from the interior surface of the primary body bottom structure 113. The normal positioning member 140 would move in a directly parallel to the normal axis 194, as the normal engaging surfaces guide the movement of the normal positioning member 140. More specifically, the normal positioning member side panel 142 slides against the primary body top flange interior edge 117 and each normal positioning member guide feature guide surface 154 slides against a respective primary body top flange lateral edge 119.

The upward motion of the normal positioning member 140 is limited by the translative positioning and locking control member base flange top surface 172 of the translative positioning and locking control member 160. The translative positioning and locking control member base flange top surface 172 engages with the primary body top flange interior normal motion limiting surface 118a of the primary body 110, limiting any further upward motion. In use, the spacing function is limited by a distance between the first vertebrae second joint surface 306 of the first vertebrae 302 and the second vertebrae second joint surface 314 of the second vertebrae 312, as illustrated in FIG. 15. The spacer insertion and expansion control mechanism assembly 200 is separated from the surgically implantable spacer 100 and withdrawn from the patient (step 424). Any potential rearward slippage of the translative positioning and locking control member 160 is stopped by the translative positioning notch retention section 134 of the respective adjacent primary body translative positioning notch 126, 127.

Once the surgically implantable spacer 100 is properly seated and expanded into a spaced configuration, the surgeon can embed bone grafts within the openings or spacings formed through the primary body 110 and/or the normal positioning member 140.

Although the exemplary illustrations present the surgically implantable spacer 100 being inserted from a posterior side, it is understood that the surgically implantable spacer 100 can be inserted from an anterior side, a left side, or a right side. The design of each surgically implantable spacer 100 can be tailored to suite a specific application. This can include the shape and size of the surgically implantable spacer 100, the location of one or more features, or any other modification to suit a specific application. The shape, size, and location of the grip features 122, 123 can be adjusted to support the desired application and installation process. The design of the surgically implantable spacer 100 can include a consideration of different span dimensions for different applications (in both retracted and expanded configurations).

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

Ref No. Description 100 surgically implantable spacer
110 primary body 112 primary body side panel
113 primary body bottom structure
114 primary body insertion end flange
115 primary body insertion end flange assembly clearance notch
116 primary body distal end panel
117 primary body top flange interior edge
118 primary body top flange
118a primary body top flange interior normal motion limiting surface
119 primary body top flange lateral edge
122 primary body proximal insertion grip feature
123 primary body distal insertion grip feature
126 primary body proximal translative positioning notch
126a primary body proximal translative positioning notch
126b primary body proximal translative positioning notch
126c primary body proximal translative positioning notch
126d primary body proximal translative positioning notch
126d primary body proximal translative positioning notch
127 primary body distal translative positioning notch
127a primary body distal translative positioning notch
127b primary body distal translative positioning notch
127c primary body distal translative positioning notch
127d primary body distal translative positioning notch
127e primary body distal translative positioning notch
128 primary body retention ridge or rib
130 translative positioning notch rising section
132 translative positioning notch seating section
134 translative positioning notch retention section
140 normal positioning member
142 normal positioning member side panel
144 normal positioning member side panel end surface
146 normal positioning member elongated axial groove
148 normal positioning member top structure
150 normal positioning member guide feature
154 normal positioning member guide feature guide surface
158 normal positioning member retention ridges
160 translative positioning and locking control member
164 translative positioning and locking control member top section
166 translative positioning and locking control member top section interior cutout
168 translative positioning and locking control member top section elongated side edge
169 translative positioning and locking control member end panel
170 translative positioning and locking control member elongated axis beltline
172 translative positioning and locking control member base flange top surface
174 translative positioning and locking control member base flange exterior surface
176 translative positioning and locking control member notch engaging projection
190 elongated axis
192 lateral axis
194 normal axis
200 spacer insertion and expansion control mechanism assembly
210 spacer insertion and spacing control handle
212 spacer insertion and spacing translative positioning element
220 spacer insertion and positioning force
222 spacer insertion and spacing translative force
300 first joint member
302 first vertebrae
304 first vertebrae first joint surface
306 first vertebrae second joint surface
310 second joint member
312 second vertebrae
314 second vertebrae second joint surface
316 second vertebrae second joint surface
320 intra-vertebral disc
322 intra-vertebral disc removal
400 a replacement spacer assembly and insertion process flow diagram
402 obtain surgically implantable spacer device components step
404 insert surgically implantable spacer thickness adjusting member step
406 insert surgically implantable spacer locking and translative positioning member step
410 prepare joint for receiving the surgically implantable spacer step
412 insert surgically implantable spacer assembly into joint step
420 slide spacer locking and translative positioning member forward step
422 spacer locking and translative positioning member axial movement raising thickness adjusting member step
424 remove insertion and expansion tool from patient step
430 embed grafts within openings formed within the surgically implantable spacer step

What is claimed is:

1. A surgically implantable spacer comprising:
a primary body having an elongated dimension extending along a longitudinal axis, a width dimension extending along a lateral axis, and a height dimension extending along a normal axis;
a primary body top flange extending generally along the lateral axis from an end of a width dimension of the primary body towards an interior of the primary body from an edge of the primary body;
a normal positioning member slideably assembled to the primary body along the normal axis;
a translative positioning and locking control member slideably assembled to the normal positioning member along the longitudinal axis; and
a normal direction interface between the translative positioning and locking control member and the primary body;
wherein the normal direction interface is configured to move the translative positioning and locking control member in a direction of the normal axis when the translative positioning and locking control member is slideably inserted into the normal positioning member in a direction of the longitudinal axis, wherein the slideable motion in the longitudinal direction is translated into a motion in the direction of the normal axis by engagement between the translative positioning and locking control member and an inclined feature in the primary body,
wherein the translative positioning and locking control member is configured to move the normal positioning member in the direction of the normal axis to a position along in a normal direction where a height dimension of a combination of the normal positioning member and the primary body is greater than the height dimension of the primary body,
wherein the primary body top flange is configured to limit the movement of the translative positioning and locking control member in the direction of the normal axis.

2. The surgically implantable spacer as recited in claim 1, wherein, when the translative positioning and locking control member is at a lowest position respective to the height dimension of the primary body, the height dimension of the combination of the normal positioning member and the primary body is one of substantially equal to or equal to the height dimension of the primary body.

3. The surgically implantable spacer as recited in claim 1, the normal positioning member further comprising a clearance having a size and shape larger than the primary body top flange,
 wherein the clearance enables movement of the normal positioning member in the direction of the normal axis passing the primary body top flange.

4. The surgically implantable spacer as recited in claim 1, the primary body further comprising a primary body insertion end flange located at an insertion end of the primary body in the elongated dimension, the primary body insertion end flange having a size and shape enabling insertion of the translative positioning and locking control member between a respective end of the primary body insertion end flange and an interior surface of the primary body top flange when inserted in a direction of the longitudinal axis.

5. The surgically implantable spacer as recited in claim 1, the inclined feature of the normal direction interface further comprising a series of translative positioning notches integral with the primary body, the series of translative positioning notches being in an inclined arrangement.

6. The surgically implantable spacer as recited in claim 1, further comprising retention ridges formed on an external surface of at least one of the primary body and the normal positioning member.

7. The surgically implantable spacer as recited in claim 1, further comprising a sliding engagement interface provided between the translative positioning and locking control member and the normal positioning member along the longitudinal axis,
 wherein a configuration of the sliding engagement interface enables a sliding movement along the longitudinal axis, while refraining from movement respective to one another along the normal axis.

8. The surgically implantable spacer as recited in claim 1, further comprising at least one insertion grip feature provided on the primary body.

9. A surgically implantable spacer comprising:
 a primary body having an elongated dimension extending along a longitudinal axis, a width dimension extending along a lateral axis, and a height dimension extending along a normal axis, the primary body including a pair of sidewalls, each sidewall extending upward from opposite edges of a base wall along the elongated dimension thereof;
 a primary body top flange extending generally along the lateral axis from a respective sidewall of the pair of sidewalls towards an interior of the primary body;
 a normal positioning member slideably assembled to the primary body along the normal axis;
 a translative positioning and locking control member slideably assembled to the normal positioning member along the longitudinal axis; and
 a normal direction interface between the translative positioning and locking control member and the primary body;
 wherein the normal direction interface is configured to move the translative positioning and locking control member in a direction of the normal axis when the translative positioning and locking control member is slideably inserted into the normal positioning member in a direction of the longitudinal axis, wherein the slideable motion in the longitudinal direction is translated into a motion in the direction of the normal axis by engagement between the translative positioning and locking control member and an inclined feature in the primary body,
 wherein the translative positioning and locking control member is configured to move the normal positioning member in the direction of the normal axis,
 wherein the primary body top flange is configured to limit the movement of the translative positioning and locking control member in the direction of the normal axis.

10. The surgically implantable spacer as recited in claim 9, wherein, when the translative positioning and locking control member is at a lowest position respective to the height dimension of the primary body, the height dimension of the combination of the normal positioning member and the primary body is one of substantially equal to or equal to the height dimension of the primary body.

11. The surgically implantable spacer as recited in claim 9, the normal positioning member further comprising a clearance having a size and shape larger than the primary body top flange,
 wherein the clearance enables movement of the normal positioning member in the direction of the normal axis passing the primary body top flange.

12. The surgically implantable spacer as recited in claim 9, the primary body further comprising a primary body insertion end flange located at an insertion end of the primary body in the elongated dimension, the primary body insertion end flange having a size and shape enabling insertion of the translative positioning and locking control member between a respective end of the primary body insertion end flange and an interior surface of the primary body top flange when inserted in a direction of the longitudinal axis.

13. The surgically implantable spacer as recited in claim 9, the inclined feature of the normal direction interface further comprising a series of translative positioning notches integral with the primary body, the series of translative positioning notches being in an inclined arrangement.

14. The surgically implantable spacer as recited in claim 9, further comprising retention ridges formed on an external surface of at least one of the primary body and the normal positioning member.

15. The surgically implantable spacer as recited in claim 9, further comprising a sliding engagement interface provided between the translative positioning and locking control member and the normal positioning member along the longitudinal axis,
 wherein a configuration of the sliding engagement interface enables a sliding movement along the longitudinal axis, while refraining from movement respective to one another along the normal axis.

16. The surgically implantable spacer as recited in claim 9, further comprising at least one insertion grip feature provided on the primary body.

17. A surgically implantable spacer comprising:
 a primary body comprising:
  a first primary body side panel, a second primary body side panel being substantially parallel to the first primary body side panel a primary body distal end panel extending between a distal end of the first primary body side panel and a distal end the second primary body side panel, and a primary body insertion end flange having a first portion extending inward from an insertion end of the first primary body side panel and a second portion extending inward from an insertion end the second primary body side panel, a first series of primary body proximal translative positioning notches proximate an interior surface of the first primary body side panel at a location adjacent to the insertion end of the first primary body side panel, a second series of primary body proximal translative positioning notches proximate an interior surface of the second primary body side panel at a location adjacent to the insertion end of the second primary body side panel, a first series of primary body distal translative positioning notches proximate the interior surface of the first primary body side panel at a location adjacent to the distal end of the first primary body side panel, and a second series of primary body distal translative positioning notches proximate the interior surface of the second primary body side panel at a location adjacent to the distal end of the second primary body side panel;

a normal positioning member comprising:
 a normal positioning member top panel,
 a pair of normal positioning member side panels extending from the normal positioning member top panel in an orientation that is substantially perpendicularly to the normal positioning member top panel, and
 a normal positioning member elongated formation extending on an interior surface of each normal positioning member side panel of the pair of normal positioning member side panels in a longitudinal direction; and a translative positioning and locking control member comprising:
 a translative positioning and locking control member body,
 a translative positioning member elongated formation extending on an exterior elongated surface of the translative positioning and locking control member body, each control member body laterally positioning member elongated formation being located, sized and shaped to slideably engage with the laterally positioning member elongated formation on each respective laterally positioning member side panel of the pair of laterally positioning member side panels,
 a series of translative positioning and locking control member notch engaging projections, each translative positioning and locking control member notch engaging projection of the series of translative positioning and locking control member notch engaging projections being located on the translative positioning and locking control member to engage with a respective notch of the respective series of primary body distal translative positioning notches, wherein the normal positioning member normally is slideably assembled to the primary body providing a sliding translative motion between the laterally positioning member and the primary body in a generally transverse direction, wherein each control member body laterally positioning member elongated formation is slideably assembled to the respective normal positioning member elongated formation;

wherein each translative positioning and locking control member notch engaging projection of the series of translative positioning and locking control member notch engaging projections engages with the translative positioning and locking control member to engage with a respective notch of the respective series of primary body distal translative positioning notches.

18. The surgically implantable spacer as recited in claim 17, wherein, when the translative positioning and locking control member is at a lowest position respective to the height dimension of the primary body, the height dimension of the combination of the normal positioning member and the primary body is one of substantially equal to or equal to the height dimension of the primary body.

19. The surgically implantable spacer as recited in claim 17, the normal positioning member further comprising a clearance having a size and shape larger than the primary body top flange,
 wherein the clearance enables movement of the normal positioning member in the direction of the normal axis passing the primary body top flange.

20. The surgically implantable spacer as recited in claim 17, the normal direction interface further comprising a series of translative positioning notches integral with the primary body, the series of translative positioning notches being in an inclined arrangement.

* * * * *